(12) United States Patent
Hubbell et al.

(10) Patent No.: US 7,592,009 B2
(45) Date of Patent: Sep. 22, 2009

(54) POLYPEPTIDE LIGANDS FOR TARGETING CARTILAGE AND METHODS OF USE THEREOF

(75) Inventors: Jeffrey A. Hubbell, Morges (CH); Dominique A. Rothenfluh, Lausanne (CH)

(73) Assignee: Ecole Polytechnique Federale de Lausanne (EPFL), Lausanne (CH)

( * ) Notice: Subject to any disclaimer, the term of this patent is extended or adjusted under 35 U.S.C. 154(b) by 142 days.

(21) Appl. No.: 11/545,819

(22) Filed: Oct. 10, 2006

(65) Prior Publication Data

US 2008/0118523 A1 May 22, 2008

(51) Int. Cl.
*A61K 39/00* (2006.01)
*A61K 38/00* (2006.01)
*A61K 38/04* (2006.01)

(52) U.S. Cl. ............... 424/184.1; 424/185.1; 514/2; 514/17; 530/329

(58) Field of Classification Search ............... None
See application file for complete search history.

(56) References Cited

U.S. PATENT DOCUMENTS

| | | | |
|---|---|---|---|
| 5,142,047 | A | 8/1992 | Summerton et al. |
| 5,185,444 | A | 2/1993 | Summerton et al. |
| 5,227,165 | A | 7/1993 | Domb et al. |
| 5,410,016 | A | 4/1995 | Hubbell et al. |
| 5,874,500 | A | 2/1999 | Rhee et al. |
| 6,022,564 | A | 2/2000 | Takechi et al. |
| 6,090,925 | A | 7/2000 | Woiszwillo et al. |
| 6,224,794 | B1 | 5/2001 | Amsden et al. |
| 2003/0233675 | A1 * | 12/2003 | Cao et al. .............. 800/279 |
| 2004/0123343 | A1 * | 6/2004 | La Rosa et al. ......... 800/278 |
| 2004/0214272 | A1 * | 10/2004 | La Rosa et al. ......... 435/69.1 |

FOREIGN PATENT DOCUMENTS

EP 1 319 669 A2 6/2003
WO WO0181581 A2 * 11/2001

OTHER PUBLICATIONS

Yokoyama1 and Ramakrishnan. Improved biological activity of a mutant endostatin containing a single amino-acid substitution. British Journal of Cancer (2004) 90, 1627-1635.*
Aina et al. Therapeutic cancer targeting peptides. Biopolymers. 2002;66(3);184-99.*
Arap et al., "Steps Toward Mapping the Human Vasculature by Phage Display," Nature Medicine, vol. 8, No. 2, pp. 121-127, Feb. 2002.
Bae et al., "Preparation and Biological Characterization of Polymeric Micelle Drug Carriers with Intracellular pH-Triggered Drug Release Property: Tumor Permeability, Controlled Subcellular Drug Distribution, and Enhanced in Vivo Antitumor Efficacy," Bioconjugate Chem, vol. 16, No. 1, pp. 122-130, 2005.
Boder et al., "Yeast Surface Display for Screening Combinatorial Polypeptide Libraries," Nature Biotechnology, vol. 15, No. 6, pp. 553-537, Jun. 1997.
Devalapally et al., "Poly(ethylene oxide)-Modified Poly(beta-amino ester) Nanoparticles as a pH-Sensitive System for Tumor-Targeted Delivery of Hydrophobic Drugs: Part 3. Therapeutic Efficacy and Safety Studies in Ovarian Cancer Xenograft Model," Cancer Chemother Pharmacol, vol. 59 pp. 477-484, 2007.
Duncan, "The Dawning Era of Polymer Therapeutics," Nature Reviews, Drug Discovery, vol. 2, pp. 347-360, May 2003.
Hern et al., "Incorporation of Adhesion Peptides into Nonadhesive Hydrogels Useful for Tissue Resurfacing," Journal of Biomedical Research, vol. 39, pp. 266-276, 1998.
Horisawa et al., "Prolonged Anti-Inflammatory Action of DL-Lactide/Glycolide Copolymer Nanospheres Containing Betamethasone Sodium Phosphate for an Intra-Articular Delivery System in Antigen-Induced Arthritic Rabbit," Pharmaceutical Research, vol. 19, No. 4, pp. 403-410, Apr. 2002.
Horisawa et al., "Size-Dependency of DL-Lactide/Glycolide Copolymer Particulates for Intra-Articular Delivery System on Phagocytosis in Rat Synovium," Pharmaceutical Researach, vol. 19, No. 2, pp. 132-139, Feb. 2002.
Kashiwagi et al., "TIMP-3 is a Potent Inhibitor of Aggrecanase 1 (ADAM-TS4) and Aggrecanase 2 (ADAM-TS5)," The Journal of Biological Chemistry, vol. 276, No. 16, pp. 12501-12504, Apr. 2001.
Kay et al., "Screening Phage-Displayed Combinatorial Peptide Libraries," Methods, vol. 24, No. 3 pp. 240-246, 2001.
Kolonin et al., "Reversal of Obesity by Targeted Ablation of Adipose Tissue," Nature Medicine, vol. 10, No. 6, pp. 625-632, Jun. 2004.
Kolonin et al., "Synchronous Selection of Homing Peptides for Multiple Tissues by in Vivo Phage Display," The FASEB Journal, vol. 20, No. 7, pp. E99-E-107, May 2006.
Lam et al., "The "One-Bead-One-Compound" Combinatorial Library Method," Chemical Reviews, vol. 97, No. 2, pp. 411-448, 1997.
Langer et al., "Optimization of the Preparation Process for Human Serum Albumin (HAS) Nanoparticles," International Journal of Pharmaceutics, vol. 257, pp. 169-180, 2003.
Lee et al., "Identification of Synovium-Specific Homing Peptides by In Vivo Phage Display Selection," Arthritis Rheumatism, vol. 46, No. 8, pp. 2109-2120, Aug. 2002.
Lu et al., "Design of Novel Bioconjugates for Targeted Drug Delivery," Journal of Controlled Release, vol. 78, pp. 165-173, 2002.
Lutolf et al., "Repair of Bone Defects Using Synthetic Mimetics of Collagenous Extracellular Matrices," Nature Biotechnology, vol. 21, pp. 513-518, May 2003.
Lutolf et al., "Synthesis and Physicochemical Characterization of End-Linked Poly(ethylene glycol)-co-peptide Hydrogels Formed by Michael-Type Addition," Biomacromolecules, vol. 4, No. 3, pp. 713-722, 2003.
Madry et al., "Recombinant Adeno-Associated Virus Vectors Efficiently and Persistently Transduce Chondrocytes in Normal and Osteoarthritic Human Articular Cartilage," Human Gene Therapy, vol. 14, No. 4, pp. 393-402, Mar. 1, 2003.

(Continued)

*Primary Examiner*—Maher M Haddad
(74) *Attorney, Agent, or Firm*—Dardi & Associates, PLLC

(57) ABSTRACT

Ligands that specifically bind to articular cartilage tissues are disclosed, including uses for targeting therapeutics towards articular cartilage tissue and new materials for articular cartilage. The ligands are effective in vivo to target therapeutic materials to articular cartilage.

18 Claims, 5 Drawing Sheets

OTHER PUBLICATIONS

Negro et al., "Recombinant Human TIMP-3 from *Escherichia coli*: Synthesis, Refolding, Physico-Chemical and Functional Insights," Protein Engineering, vol. 10, No. 5, pp. 593-599, 1997.

Nishiyama et al., "Novel Cisplatin-Incorporated Polymeric Micelles Can Eradicate Solid Tumors in Mice," Cancer Research, vol. 63, No. 24, pp. 8977-8983, Dec. 15, 2003.

Park et al., "Photopolymerized Hyaluronic Acid-Based Hydrogels and Interpenetrating Networks," Biomaterials, vol. 24, pp. 893-900, 2003.

Pasqualini et al., "Organ Targeting in Vivo Using Phage Display Peptide Libraries," Nature, vol. 380, pp. 364-366, Mar. 1996.

Phillips et al., "Liposome-Incorporated Corticosteroids. II. Therapeutic Activity in Experimental Arthritis," Annals of the Rheumatic Diseases vol. 38, No. 6, pp. 553-557, 1979.

Quinn et al., "Static Compression is Associated with Decreased Diffusivity of Dextrans in Cartilage Explants," Archives of Biochemistry and Biophysics, vol. 384, No. 2, pp. 327-334, Dec. 2000.

Quinn et al., "Static Compression of Articular Cartilage Can Reduce Solute Diffusivity and Partitioning: Implications for the Chondrocyte Biological Response," Journal of Biomechanics, vol. 34, No. 11, pp. 1463-1469, 2001.

Rehor et al., "Oxidation-Sensitive Polymeric Nanoparticles," Langmuir, vol. 21, No. 1, pp. 411-417, 2005.

Smith et al., "Phage Display," Chemical Reviews, vol. 97, No. 2, pp. 391-410, 1997.

Staskus et al., "The 21-kDa Protein is a Transformation-Sensitive Metalloproteinase Inhibitor of Chicken Fibroblasts," The Journal of Biological Chemistry, vol. 266, No. 1, pp. 449-454, Jan. 1991.

Tobio et al., "Stealth PLA-PEG Nanoparticles as Protein Carriers for Nasal Administration," Pharmaceutical Research, vol. 15, No. 2, pp. 270-275, 1998.

Torzilli et al., "Effect of Proteoglycan Removal on Solute Mobility in Articular Cartilage," J. Biomechanics, vol. 30, No. 9, pp. 895-902, 1997.

Trentin et al., "Peptide-Matrix-Mediated Gene Transfer of an Oxygen-Insensitive Hypoxia-Inducible Factor-1α Variant for Local Induction of Angiogenesis," PNAS, vol. 103, No. 8, pp. 2506-2511, Feb. 21, 2006.

Xu et al., "Directed Evolution of High-affinity Antibody Mimics Using mRNA Display," Chemistry & Biology, vol. 9, No. 8, pp. 933-942, Aug. 2002.

Zacher et al., "A New Filamentous Phage Cloning Vector: fd-tet," Gene vol. 9, pp. 127-140, 1980.

Duncan, "Designing Polymer Conjugates as Lysosomotropic Nanomedicines", Biochemical Society Transactions, 35 (1): 56-60 (Feb. 2007).

Kiick, "Polymer Therapeutics", Science, 317(5842):1182-1183 (Aug. 31, 2007).

Rothenfluh et al., "Biofunctional Polymer Nanoparticles for Intra-articular Targeting and Retention in Cartilage", Nature Materials, 7(3): 248-254 (Mar. 2008).

Setton, "Reservoir Drugs", Nature Materials, 7(3): 172-174 (Mar. 2008).

Yake et al., "Localized Functionalization of Individual Colloidal Carriers for Cell Targeting and Imaging", Biomacromolecules, 8(6):1958-1965 (Jun. 2007).

* cited by examiner

US 7,592,009 B2

POLYPEPTIDE LIGANDS FOR TARGETING CARTILAGE AND METHODS OF USE THEREOF

TECHNICAL FIELD

The technical field of the invention is generally related to delivery of therapeutic agents to cartilage tissues using polypeptides that specifically bind cartilage.

BACKGROUND

Cartilage lesions are common and can pose difficulties both in diagnosis and treatment. A lesion can either be a defect or a focal cartilage degradation without visible disruption of the cartilage matrix. Such lesions can result from an injury as in sports, disease, or aging. The prognosis of an articular cartilage defect varies according to age, mechanism of injury, site, size, associated injuries and treatment received.

SUMMARY OF THE INVENTION

The invention, however, provides treatments for cartilage injury. Some aspects of the inventions are substantially pure polypeptides comprising an amino acid sequence of WYRGRL (SEQ ID NO:1), DPHFHL (SEQ ID NO:2), or RVMLVR (SEQ ID NO:3), or a conservative substitution thereof, or a nucleic acid encoding the same. Such polypeptides specifically bind cartilage tissue. Such polypeptides may also include a therapeutic agent.

Some inventive methods are related to treating cartilage of a mammal comprising administering to the mammal a pharmaceutically acceptable composition that comprises a nucleic acid encoding a polypeptide that specifically binds a cartilage tissue. Such polypeptide may also encode a therapeutic agent that, for example, treats a joint or tissue.

Other aspects of the invention relate to a delivery system for delivering a therapeutic agent comprising: a substantially purified preparation that comprises a pharmaceutically acceptable excipient, a therapeutic agent, and a polypeptide ligand comprising an amino acid sequence in the group consisting of SEQ ID NO:1, SEQ ID NO:2, SEQ ID NO:3, and conservative substitutions thereto. The polypeptide ligands may specifically bind to cartilage tissue for targeted delivery of the therapeutic agent to cartilage tissues. The therapeutic agent may comprise, for example, a drug, a visualization agent, or a therapeutic polypeptide. The delivery system may include, for example, a collection of nanoparticles having an average diameter of between about 10 nm and about 200 nm, wherein the nanoparticles comprise the therapeutic agent and the polypeptide ligand.

Other embodiments relate to a biomaterial comprising a polymer and a substantially pure polypeptide comprising an amino acid sequence of SEQ ID NO:1, SEQ ID NO:2, SEQ ID NO:3, or a conservative substitution thereof, wherein the polypeptide specifically binds to cartilage tissue and the polymer is free of amino acids and has a molecular weight of at least 400. A variant of WYRGRL (SEQ ID NO:1) is WYRGRLC (SEQ ID NO:4), with the C-terminal residue being used as a chemical linker.

DETAILED DESCRIPTION

Introduction

Figure 1A:
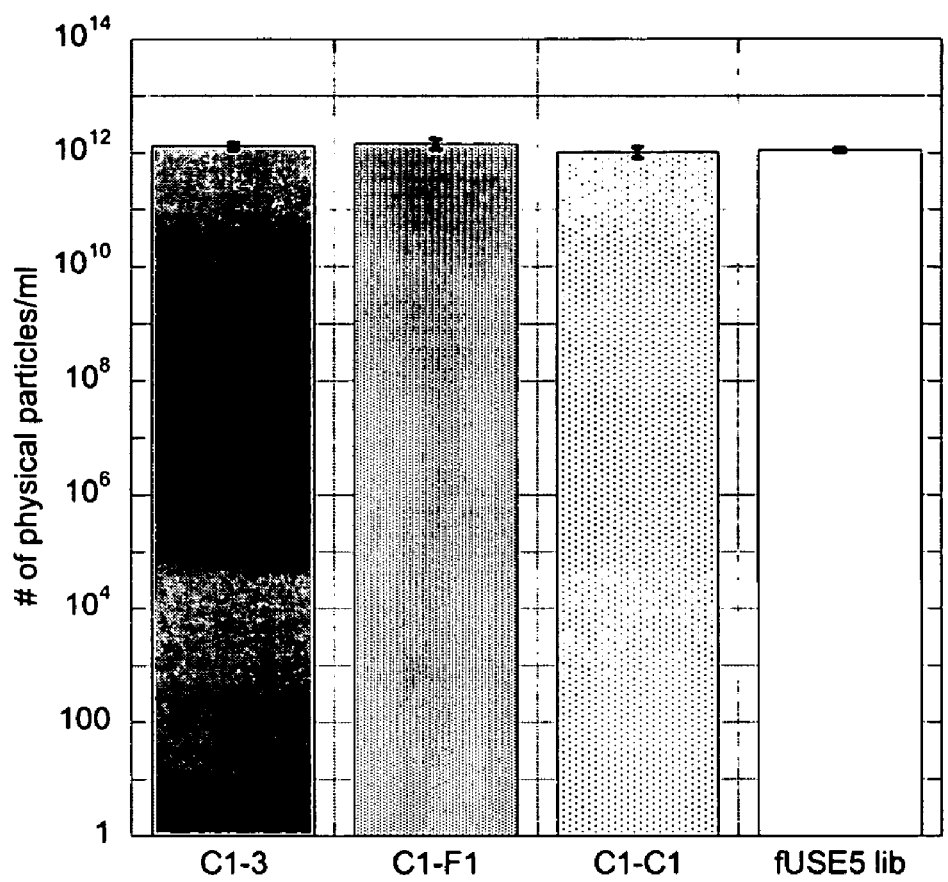
FIG. 1a is a bar graph that shows amplification of three phage clones identified by biopanning and demonstrates that they all grow at equal rates comparable to the random library. Final selection of C1-3 was therefore not affected by differences in growth during amplification.

Ligands that specifically bind to articular cartilage tissues have been discovered. These articular cartilage tissue-binding ligands have given rise to new techniques to target therapeutics towards articular cartilage tissue and new materials for treatment of articular cartilage defects. The ligands are effective in vivo to target therapeutic materials to articular cartilage.

Three of the cartilage tissue-binding ligands are polypeptides with the amino acid sequence of WYRGRL (SEQ ID NO:1), DPHFHL (SEQ ID NO:2), or RVMLVR (SEQ ID NO:3). Other ligands are polypeptides with sequences that have conservative substitutions of one of SEQ ID NOs. 1, 2, or 3. Ligand is a term that refers to a chemical moiety that has specific binding to a target molecule. A target refers to a predetermined molecule, tissue, or location that the user intends to bind with the ligand. Thus targeted delivery to a tissue refers to delivering a molecule to the intended target tissue; a therapeutic agent delivered to a target may be intended to act on the target itself or on some other molecule or cell, e.g., a cell or tissue that is near the target.

One application of the cartilage tissue-binding ligands is for targeting therapeutic agents to articular cartilage, commonly referred to as intra-articular drug delivery when drugs are delivered. Intra-articular drug delivery has been termed a major challenge due to the short residence times of intra-articular injected drugs. Drugs injected by themselves tend to diffuse away rapidly or be otherwise rapidly taken up into the circulation, thus causing low bioavailability of the drug at the cartilage and unwanted systemic effects. Despite sustained-release drugs, only a few reports exist on the intra-articular use of any sustained-release formulations[20-26]. Mostly albumin and poly (lactic-co-glycolic acid) (PLGA) have been used as biocompatible and biodegradable polymers for this purpose either in the form of gels[22] or as microspheres[23-26]. Such approaches rely, however, on degradation over time to achieve sustained-release within the joint, a strategy that is limited by the properties of available biomaterials, and which makes the drugs available only when the material degrades. Targeting the delivery system to articular cartilage with tissue-binding ligands makes the tissue itself a reservoir for drug release to the site of the disease process as opposed to release in the joint cavity.

The cartilage tissue-binding ligands are also useful to bind cartilage tissue in vitro for diagnostic, assay, or imaging purposes. For instance, sections of tissue may be exposed to cartilage tissue-binding ligands that are also bound to a fluorescent molecule or other imaging agent to visualize the location of the cartilage tissue. Or, for instance, the cartilage tissue-binding ligands may be used in affinity chromatography to isolate the tissue.

In some aspects, therefore, articular cartilage tissue-binding ligands described herein enable new techniques for controlled release by enabling sustained localization through specific binding to cartilage, and their accompanying formulations increase intra-articular bioavailability of delivered drugs or other therapeutic agents, which is beneficial for various disease processes, e.g., those involving the synovium such as rheumatoid arthritis or inflammation in clinically manifest osteoarthritis. Because convective transport of solutes into cartilage is impaired due to the inherent properties of this tissue[27,28], the bioavailability of drugs in the cartilage matrix, which is the primary site of the disease process in osteoarthritis, can be enhanced by sustained release systems that reside in the matrix itself. Targeting of the cartilage matrix as described herein is therefore useful for general intra-articular therapeutic agent delivery, such as targeting of the cartilage matrix for delivery of therapeutic agents to treat cartilage degradation in osteoarthritis and protect cartilage in conditions like rheumatoid arthritis, bacterial and reactive arthritis.

The cartilage tissue-binding ligands are thus useful to direct therapeutic agents to a target. A therapeutic agent refers to a molecule for delivery to a target to accomplish a desirable medical or scientific function, and the term includes drugs and imaging agents. Examples of therapeutic agents are matrix metalloproteinase (MMP) inhibitors, aggrecanase inhibitors, COX-inhibitors and other non-steroidal anti-inflammatory drugs (NSAIDs), glucosamin, diacerhein, methotrexate, steroids, immunosuppressing drugs (rapamycin, cyclosporine), protein therapeutics (growth factors, tissue inhibitors of matrix metalloproteinases), and oligonucleotides (e.g., siRNA, shRNA, miRNA). Examples of imaging agents are fluorescent markers, radio-opaque materials, magnetic resonance imaging contrast agents, x-ray imaging agents, radiopharmaceutical imaging agents, ultrasound imaging agents, and optical imaging agents.

Ligand Discovery and Experimental Data

The development of phage display of random peptides on the minor coat proteins (pIII) of bacteriophages has allowed use of affinity purification, in a process called biopanning[5], to identify specific peptides for precise targeting of multiple tissues, both in vitro[6] and in vivo in animals and even humans[7-9]. As an example, Arap et al. have succeeded in mapping the human vasculature and specifically targeting the microvasculature of adipose tissue in mice[10]. Another study identified a synovium-specific homing peptide by phage display. Human synovial grafts were transplanted into SCID mice and biopanning was carried out in vivo which resulted in the identification of phages with homing peptides specific for the microvascular endothelium of synovial tissue[11].

In order to identify peptide sequences which bind to the articular cartilage extra-cellular matrix, it should first be appreciated that an in vivo approach to biopanning must address the challenges presented by the dense organization of extra-cellular matrix molecules. Indeed, the collagen II fiber network of articular cartilage has a reported mesh size of 60 nm in the superficial zone[12] and largest gaps between the side chains of proteoglycan aggregates have been described to be as low as 20 nm[13]. Biopanning was therefore carried out not in vivo, but instead was adpated for use with ex vivo materials. Specifically, sliced bovine cartilage was used, wherein the extra-cellular matrix was exposed for affinity purification of binding phage virions.

Materials

The phage display library fUSE5/6-mer based on filamentous phage strain fd-tet was received from the University of Missouri, Columbia. Cartilage grafts, synovial fluid and synovial membrane were harvested from bovine shoulders obtained from the local slaughterhouse. Cartilage grafts were stored in 0.1% sodium azide and protease inhibitors at 4° C. and used within 72 hours. Buffers and solutions used for phage-display screening: Blocking solution (0.1M $NaHCO_3$, 1% BSA, pH 8.5), wash buffer (PBS, Tween 20 0.1-1%), elution solution (50 mM glycine-HCl, pH 2.0), neutralisation buffer (0.2M $NaHPO_4$). Solvents and reagents for nanoparticle synthesis were purchased from Sigma-Aldrich (Buchs, Switzerland). All peptides (synthesis chemicals from Novabiochem, Läutelfingen, Switzerland) were synthesized on solid resin using an automated peptide synthesizer (CHEM-SPEED PSW 1100, Augst, Switzerland) with standard F-moc chemistry. Purification was performed on a Waters ultrapurification system using a Waters ATLANTIS $dC_{18}$ semi-preparative column and peptides collected according to their molecular mass analyzed by time-of-flight (TOF) mass spectrometry.

Screening of Phage-Displayed Combinatorial Peptide Library and Binding Assays

Peptides for binding to the articular cartilage matrix were selected by exposing a fUSE5/6-mer library to bovine cartilage grafts, which provided $6.4 \times 10^7$ different phage clones with 6-amino acid linear-peptide inserts displayed on the minor coat protein of filamentous phage[5,18]. Cartilage grafts were harvested with 8 and 4 mm biopsy cutters (two-sided surface 1 $cm^2$ and 0.25 $cm^2$). A slice with the intact articular surface was removed to expose the phages only to the cartilage matrix below the surface. Affinity selection was preformed in polystyrene 48-well plates, which were blocked for nonspecific adhesion with a blocking solution containing 1% BSA for 2 hours prior to screening. A total of 5 screening rounds was carried out. In the first round $10^{13}$ and in subsequent rounds $10^{12}$ phage virions per ml were exposed to the cartilage graft, washed with PBS/Tween 20 and eluted at low pH. While the first round was supposed to give a high yield at low stringency, subsequent rounds were carried out with increasing stringency to select stronger binders. Conditions were increased from 4 hours of binding at RT and washing with PBS/0.1% Tween to 30 minutes binding at 37° C. with 220 RPM, washing with PBS/1% Tween 20 and the cartilage surface decreased from 1 $cm^2$ to 0.25 $cm^2$ in round five. Eluted phage was amplified overnight in E. coli strain TG1 in 2×YT medium and purified by two times PEG/NaCl (2M, 25%) precipitation. In the first round of screening, negative screens against the intact articular surface as well as synovial fluid (50% diluted in PBS to lower viscosity) were carried out in order to eliminate phages binding to these targets. Quantitative titer counts were obtained by spot titering of 15 µl of phage/bacterial culture onto LB-agar/tetracyclin plates and are given in transducing units(TU)/ml. The polypeptide sequences of affinity selected phage specific to the articular cartilage matrix was determined by DNA sequencing (Microsynth AG, Balgach, Switzerland) using the sequencing primer 5'-CAT GTA CCG TAA CAC TGA G (SEQ ID NO:5). Binding specificity was determined by exposing selected phage clones ($10^8$ TU/ml) to articular cartilage (0.25 $cm^2$) with and without synovial fluid, to synovial membrane (3×4 mm, 0.24 $cm^2$) and to polystyrene after blocking. Titer counts were obtained by spot titering. Competetive binding was probed by exposing a mix of selected phage clones and fUSE5/6-mer library (each $10^8$ TU/ml) in the presence of synovial fluid to articular cartilage for 30 min. at 37° C., 220 RPM and washed with PBS/1% Tween 20. The phage clones were identified by DNA sequencing and the corresponding titer counts calculated. For comepetetive binding against free polypeptide or nanoparticles and to obtain a dose-response curve, $10^8$ TU/ml of phage and its free polypeptide in different concentrations or nanoparticles were mixed, exposed to articular cartilage and titer counts determined. All experiments have been carried out in triplicate and repeated for confirmation.

Nanoparticle Synsthesis

Poly(propylene sulfide) nanoparticles were prepared as described elsewhere[14]. Briefly, for nanoparticles between 30 and 40 nm, a monomer emulsion is prepared by dissolving 1.6% (w/v) of Pluronic F-127 (MW 12600) in 10 ml of degassed, double-distilled and filtered water. The system is continuously stirred and purged with argon for 60-90 min. Propylene sulfide is added at a Pluronics/monomer ratio of 0.4 (w/w). The initiator, pentaerythritol tetrathioester (TTE) (synthesized as described previously[14]), is deprotected by mixing with a molar equivalent of 0.5M sodium methanoate and stirred under argon for 5 minutes. The deprotected initiator is then added to the emulsion. Five minutes later, 60 µl of diaza[5.4.0]bicycloundec-7-ene (DBU) is added and the reaction stirred under inert conditions for 6 hours. Exposure to air yields disulfide crosslinking of the particle core. Particles are subsequently purified from remaining monomers and base by 2 days of repeated dialysis against ultrapure water through a membrane with a MWCO of 6-8 kDa (Spectra/Por). Free Pluronic F-127 is removed in a second dialysis step through 300 kDa membranes. Particle size is measured after dialysis by dynamic light scattering (ZETASIZER NANO ZS, Malvern Instruments, Malvern, UK). For preparation of surface-functionalized nanoparticles, polypeptides are conjugated to Pluronics-F127 prior to nanoparticle synthesis. In order to derivatize Pluronics F-127 with vinyl sulfone, 400 ml of toluene and 15 g of Pluronic F-127 were introduced in a 3-neck round bottom flask connected to a Soxhlett filled with glass wool and dry molecular sieves and a cooling tube. Pluronic was dried azeotropically during 4 h. The dried Pluronic in toluene was cooled in an ice-bath and sodium hydride was added in a 5 equimolar excess compared with Pluronic-OH-groups. The reaction was stirred for 15 minutes and divinyl sulfone was added in a 15 molar excess and the reaction was carried out in the dark for 5 days at RT under argon. The reaction solution was filtrated through a celite filter cake, concentrated by rotary evaporation and then precipitated 5 times in ice-cold diethylether. The polymer was dried under vacuum and stored under argon at −20° C. Derivatization was confirmed with $^1$H-NMR (CDCl$_3$):=1.1 (m, PPG CH$_3$), 3.4 (m, PPG CH), 3.5 (m, PPG CH$_2$), 3.65 (m, PEG CH$_2$), 6.1 and 6.4 (d, 1H each, CH$_2$=CH—SO$_2$—), 6.85 (q, $^1$H, CH$_2$=CH—SO$_2$—) ppm. A degree of end group derivatization of 88% was determined by $^1$H-NMR. All polypeptides were acetylated at the N-terminus to prevent reaction with the ∝-amine and synthesized with a cysteine at the C-terminus to be conjugated to Pluronics-di-vinyl sulfone by Michael-type addition via the free thiol[29]. For conjugation, 1.6 mM Pluronics-di-vinyl sulfone is stirred in triethanolamine buffer at pH 8.5 until it is completely dissolved and 2 mM of polypeptide is added and stirred for 3 hours at RT. Conjugation is confirmed by absent vinyl sulfone peaks by $^1$H-NMR in methanol. Nanoparticles are prepared as described above with 10% surface functionalisation corresponding to a fraction of 0.16% (w/v) of conjugated Pluronic. The presence of the polypeptide on the particle is confirmed by measuring the zeta potential by dynamic light scattering (ZETASIZER NANO ZS, Malvern Instruments, Malvern, UK) after particle synthesis. The nanoparticles were fluorescently labelled with 6-iodoacetamide fluorescein (6-IAF, Molecular Probes, Eugene, Oreg.) or Alexa FLUOR 488 maleimide by adding label at 1 mg/ml of nanoparticle solution in 10 mM Tris-HCl pH 8.5 and stirred in the dark for 2 h at room temperature. Unreacted label was quenched by adding 5 mg L-Cysteine. Purification was accomplished by dialysis for 24 hours against a membrane with MWCO of 24 kDa in 5 mM PBS with two buffer shifts.

In vivo Injection

Labeled nanoparticles were injected into knee joints of 4-6 weeks old C57BL/6 mice at a concentration of 1% (w/v) in a volume of 5 µl using a 25 µl Hamilton syringe with Cheney reproducibility adapter and 30 G needles (animal experimentation protocol approved by the local review board, authorisation no. 1894). The mice were anesthetized with isoflurane. The animals were euthanized by CO$_2$-asphyxiation after 24 hours. The knee joints were harvested and freed from surrounding muscle by microdissection.

Confocal Microscopy and Image Analysis

The sections were analyzed by confocal laser scanning microscopy using a Zeiss LSM510 meta. Fluorescence was extracted by emission fingerprinting to reduce autofluorescence of cartilage tissues. The pinhole was adjusted using TETRASPECK fluorescent microspheres (Invitrogen, T14792, Carlsbad, Calif.). Images for analysis were obtained using a Zeiss 63× APOCHROMAT objective in 10 different locations per joint with a z-stack of 10 images each. Image deconvolution was accomplished by Huygens software. Image analysis was done by ImageJ.

Affinity Selection of Phage Display Library and Binding Assay

Cartilage grafts were incubated with the fUSE5 peptide on phage display library, which expressed linear 6-mer random peptides on minor coat proteins (pIII) with a diversity of 6.4×$10^7$. The sequences corresponding to the polypeptides displayed on the phage virions were determined by DNA sequencing after rounds 3 and 5 of affinity selection (panning). After round 3, sequencing did not reveal a consensus motif in the selected polypeptides. Sequencing of round 5 yielded three different phage clones C1-3 (having SEQ ID NO:1), C1-C1 (having SEQ ID NO:2) and C1-F1 (having SEQ ID NO:3), whereas C1-3 appeared in 94 out of 96 sequenced clones and C1-C1 and C1-F1 both only appeared once. To ensure that the selection of the three phage clones was not the result of differences in their amplification rates compared to other phages, overnight amplification of $10^6$ particles/ml of the three selected clones and the random fUSE5 phage library was performed in a bacterial culture. As shown in FIG. 1a, all amplification rates are equal to the rate of the random library. This suggests that the three phage clones were not selected in the panning process because of differences in their amplification speed, which would have biased the library in their favor. A competetive binding assay was carried out to assess the relative binding strength of the selected phage clones against each other. Equal amounts of the three phage clones and the random fUSE5 library were mixed and exposed to cartilage grafts (0.25 cm$^2$). The corresponding titer counts of recovered phage virions were determined by DNA sequencing of 96 colonies in triplicate. It is demonstrated in FIG. 1b that only C1-3 and C1-C1 have been recovered, thereby indicating their superior binding strength over C1-F1 and the random library. In addition, C1-3 has a higher titer count of almost one order of magnitude than C1-C1 which further demonstrates its dominant binding which was already suggested by its frequent appearance after round 5.

Figure 1B:
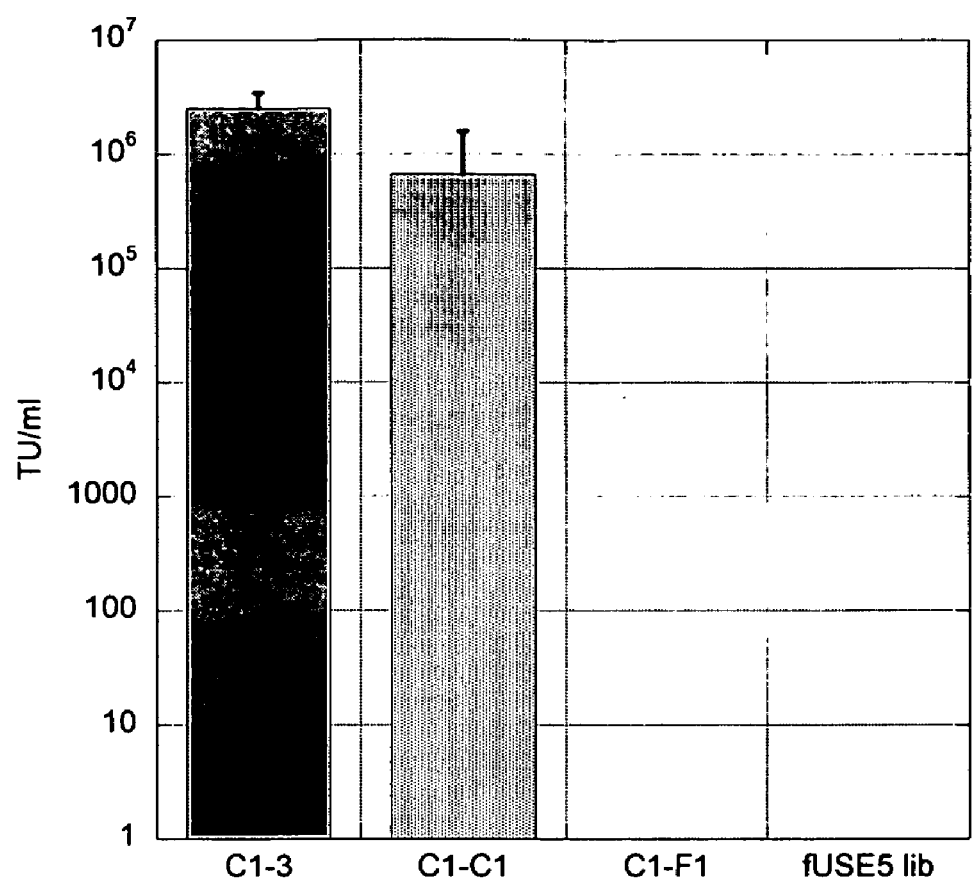
FIG. 1b is a bar graph that demonstrates the competetive binding assay in which only phage clone C1-3 and C1-C1 could be recovered.
Figure 1C:
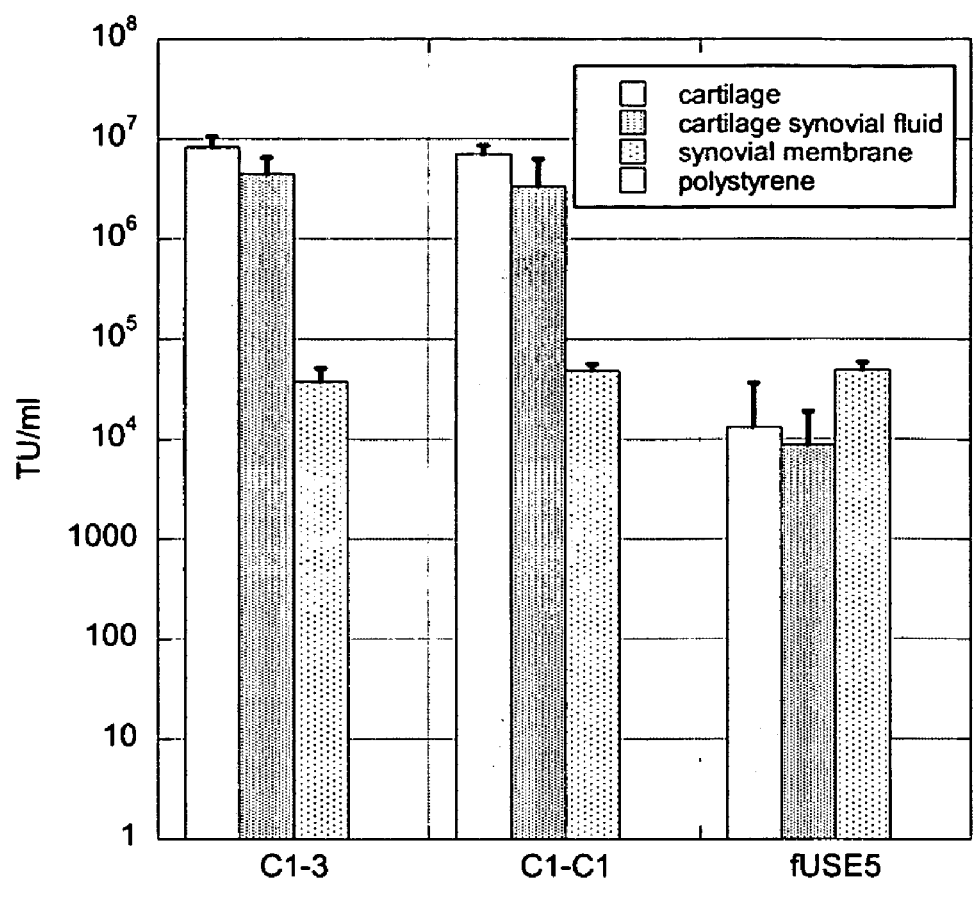
FIG. 1c is a bar graph that shows binding specificity of C1-3 and C1-C1 to articular cartilage. Binding of these phage clones to synovial membrane resulted in a lower phage recovery by two orders of magnitude, reflecting non-specific binding. Error bars indicate mean±standard deviation from three independent experiments.

The binding specificity of C1-3 and C1-C1 to articular cartilage was evaluated by exposing the phage clones to articular cartilage (0.25 cm$^2$) and synovial membrane (0.24 cm$^2$) and comparing to random binding of the fUSE5 phage library. Furthermore, the effect of the presence of synovial fluid on phage binding was probed by adding an equal volume of bovine synovial fluid to the phages, which dilutes the synovial fluid by a factor of 2. FIG. 1c shows that both C1-3 and C1-C1 exhibit specific binding to articular cartilage over synovial membrane by two orders of magnitude and that the addition of synovial fluid does not yield a significant drop in phage binding to articular cartilage. Binding of the specific phage clones to synovial membrane seems to reflect background phage binding as the random phage library fUSE5 bound to the synovial membrane to the same extent. In addition, phage titers of fUSE5 to articular cartilage were at the same level as to synovial membrane, further indicating specific binding of C1-3 and C1-C1. Phage was exposed to polystyrene wells after blocking them with BSA because it is contained in the plasticware in which affinity selection was carried out. No background phage binding to polystyrene was detectable, however.

Affinity selection of fUSE5/6-mer phage display library resulted in the discovery the phage clone C1-3 (polypeptide WYRGRL, SEQ ID NO:1) which exhibits both binding specificity to articular cartilage and dominant binding compared to other phage clones. Specific binding in the context of a polypeptide refers to the binding of the polypeptide specifically to the target of interest as opposed to other molecules.

Competetive Binding of C1-3 Against Free Polypeptid s WYRGRLC and YRLGRWC

Figure 2:
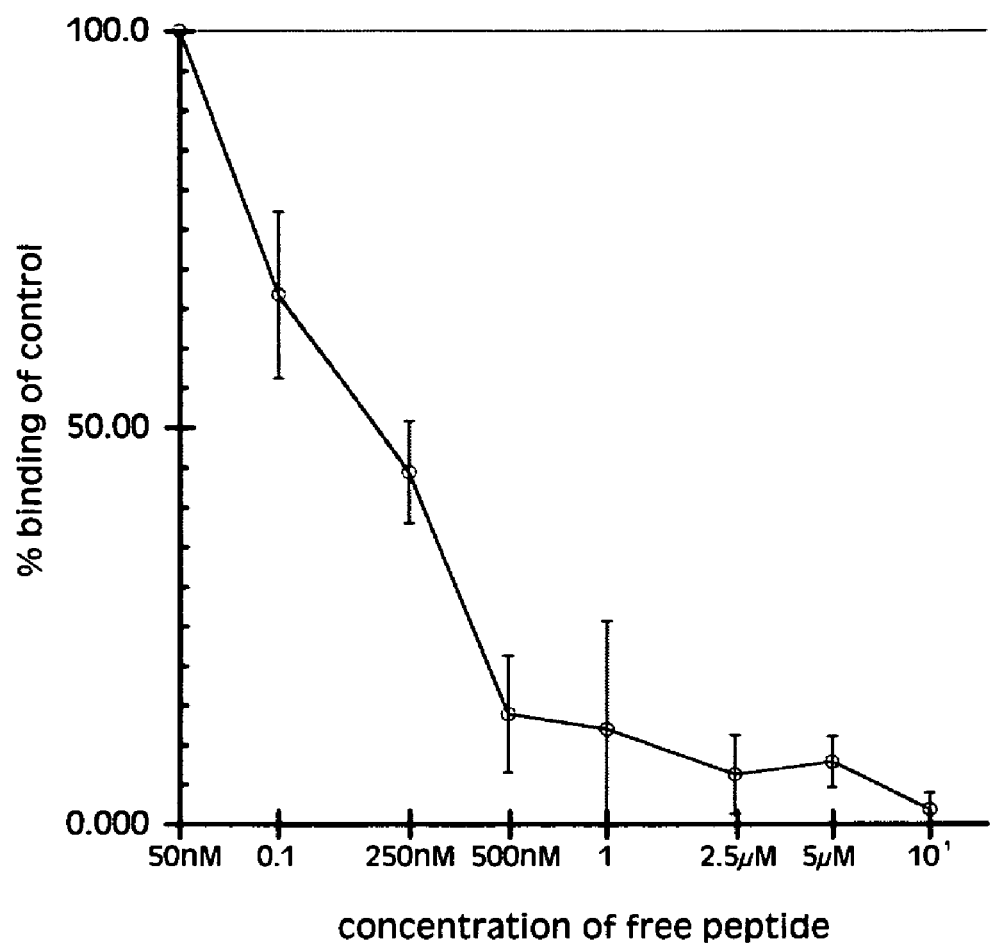
FIG. 2 is a graph showing inhibition of cartilage binding of C1-3 by the synthetic polypeptide WYRGRLC (SEQ ID NO:4). Data represents the percentage of maximal phage binding of clone C1-3 obtained in the absence of synthetic polypeptide. Error bars indicate mean±standard deviation from three independent experiments.

Based on affinity selection and the binding assays reported herein, the 6-mer polypeptide insert WYRGRL (SEQ ID NO:1) of clone C1-3 as well as its scrambled mismatch YRLGRW (SEQ ID NO:6) were synthesized on solid resin using standard Fmoc chemistry. The N-terminal amino acids are acetylated and a cysteine was added to the C-termninus of the polypeptides for bioconjugation to vinyl sulfone by Michael-type addition via the free thiol. In order to further characterize the binding properties of WYRGRLC (SEQ ID NO:4) to articular cartilage, a competetive binding assay against the phage clone C1-3 was performed by exposing the C1-3 and the WYRGRLC (SEQ ID NO:4) to the cartilage. A dose-response curve was determined by serial dilutions of the polypeptide ranging from 50 nM to 10 µM and mixing them with 10$^8$ TU/ml of phage. The titer counts of phage recovered gradually decreased by two orders of magnitude as the concentration of the free polypeptide in solution was increased (FIG. 2). An IC50 of about 200 nM can be estimated from the curve in FIG. 2.

Conjugation of Polypeptide to Pluronic F-127 and Nanoparticle Synthesis

In order to functionalize poly(propylene sulfide) (PPS) nanoparticles, Pluronic F-127 was derivatized with vinyl sulfone. The polypeptides were conjugated to Pluronic-di-vinyl sulfone via the free thiol in the C-terminal cysteine by Michael-type addition. Conjugation was confirmed by $^1$H-NMR in methanol by the absence of peaks specific to vinyl sulfone. PPS nanoparticles were then prepared by inverse emulsion polymerization with Pluronic F-127 (90%) and polypeptide-conjugated Pluronic F-127 (10%) serving as the emulsifier. Because Pluronic as the emulsifier remains on the particle surface, the conjugated polypeptide is displayed on the surface of the nanoparticles, thereby adding the targeting functionality of the polypeptide to the particles. Size measurements by dynamic light scattering (ZETASIZER NANO ZS, Malvern Instruments, Malvern, UK) revealed a size by volume of 38 nm for PPS particles displaying WYRGRLC (SEQ ID NO:4) (polydispersity index PDI 0.221), 31 nm for particles displaying YRLGRWC (SEQ ID NO:7) PDI 0.412) and 37 nm for non-conjugated PPS particles (PDI 0.212). The zeta-potential of non-conjugated PPS nanoparticles is about neutral (−2.64±8.97 mV). Due to the positive charges of the polypeptide, the zeta-potential of conjugated nanoparticles shifted to +17.8±3.45 mV, which further confirms the presence of the polypeptide on the nanoparticle surface.

Figure 3:
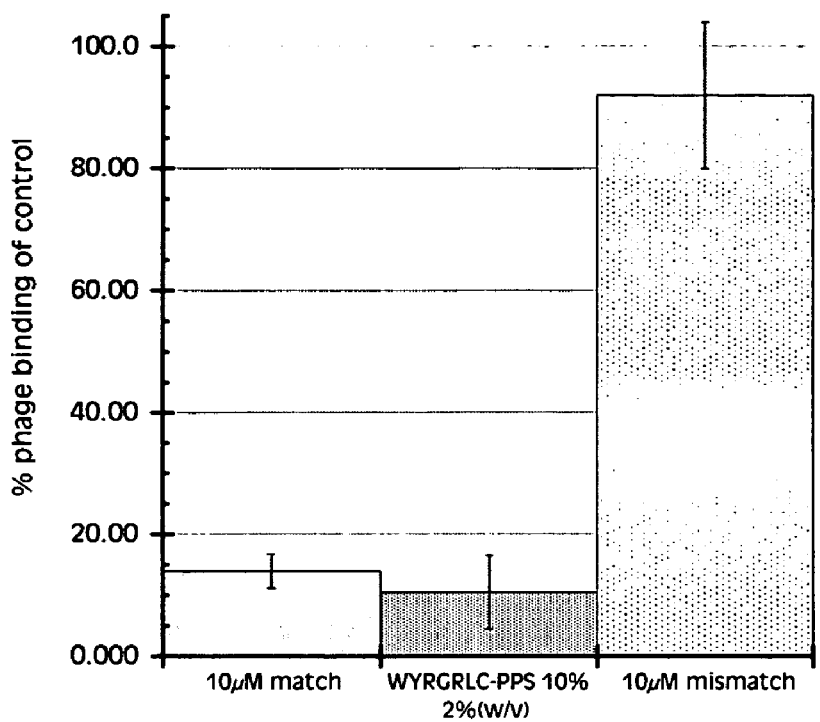
FIG. 3 is a bar graph showing inhibition of cartilage binding of C1-3 phage by 10 μM of synthetic polypeptide vs. WYRGRLC (SEQ ID NO:4)-PPS nanoparticles and 10 μM of synthetic mismatch polypeptide. WYRGRLC (SEQ ID NO:4)-PPS nanoparticles exhibit similar binding than the synthetic polypeptide, whereas the synthetic mismatch polypeptide does not result in a significant decrease of phage titer. Error bars indicate mean±standard deviation from three independent experiments.

WYRGRLC (SEQ ID NO:4)-PPS nanoparticles at 2% (w/v) were subjected to a competetive binding assay against the free polypeptides WYRGRLC (SEQ ID NO:4) and YRLGRWC (SEQ ID NO:7) at concentrations of 10 µM each. Accordingly, phage clone C1-3 was exposed to the cartilage in the presence of WYRGRLC (SEQ ID NO:4)-PPS nanoparticles, WYRGRLC (SEQ ID NO:4) or YRLGRWC (SEQ ID NO:7), and the amount of C1-3 phage binding to the cartilage relative to a control C1-3 phage without competitive inhibitors was measured. The results in FIG. 3 show that WYRGRLC (SEQ ID NO:4)-PPS nanoparticles exhibit similar binding as the corresponding free polypeptide (WYRGRLC (SEQ ID NO:4)-PPS 10.4±6% and WYRGRLC (SEQ ID NO:4) 13.9±2.8% of control), whereas the YRLGRWC (SEQ ID NO:7) did not bind competetively and thus did not result in a significant drop of phage titer (92±12% of control). Conjugated PPS nanoparticles at a degree of surface functionalisation of 10% at 2% (w/v) therefore seem to have similar binding to articular cartilage as the free polypeptide WYRGRLC (SEQ ID NO:4) at 10 µM.

Active Targeting of Articular Cartilage in vivo

Figure 4:
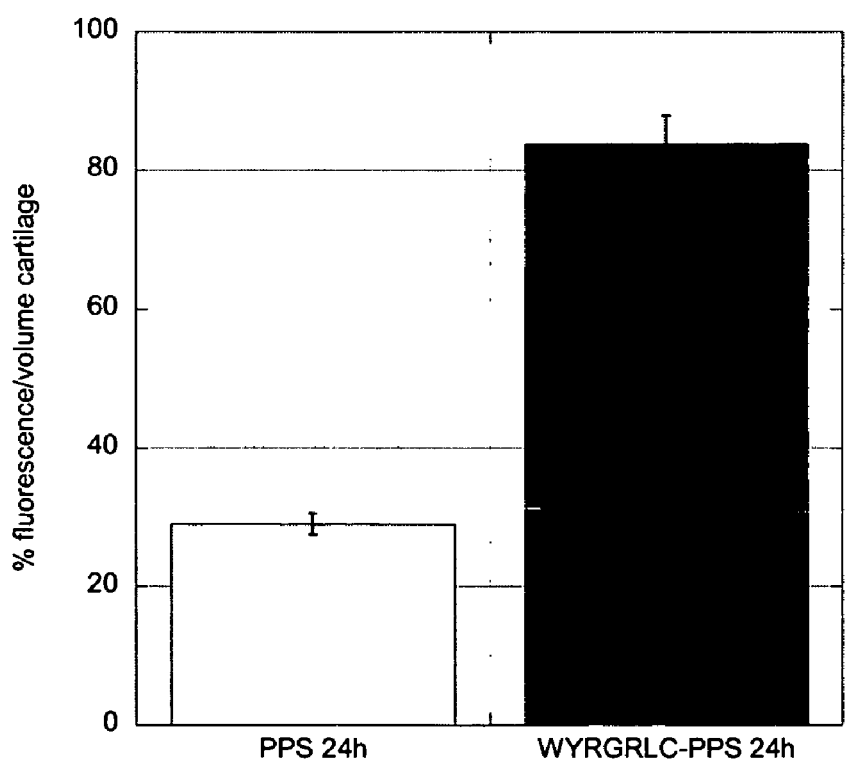
FIG. 4 is a bar graph showing relative accumulation in articular cartilage in vivo of nanoparticles decorated with WYRGRLC (SEQ ID NO:4) compared to control nanoparticles. Error bars indicate mean±standard deviation from three independent experiments.

WYRGRLC (SEQ ID NO:4)-PPS and PPS nanoparticles were labeled with 6-IAF and dialysed for 2 days with at least 2 buffer shifts to ensure that no free label is still in the solution. A volume of 5 µl of the nanoparticles was injected into the knee joints of 4-6 weeks old C57BL/6 mice. Three mice were injected with WYRGRLC (SEQ ID NO:4)-PPS in the right and PPS particles in the left knee joint. In order to do reproducible injections a 25 µl Hamilton syringe (Hamilton Europe, Bonaduz, Switzerland) with a Cheney reproducibility adapter was used for antero-lateral parapatellar injection with a 30 G needle. Cryosections which were obtained after 24 hrs were analysed by confocal laser scanning microscopy. Quantification of fluorescent dots per cartilage volume as determined by sampling of z-stacks with 10 planes in 10 different locations per joint revelead an increase in particle accumulation from 29.0±1.5% for PPS particles to 83.8±4.0% for WYRGRLC (SEQ ID NO:4)-PPS particles (FIG. 4). While there is an obvious favorable accumulation of functionalized nanoparticles in the articular cartilage matrix after 24 hours, nanoparticles accumulate in the whole joint at a concentration of 2% (w/v) and enter meniscal and ligamentous tissues in addition to the synovial membrane.

Discussion

Several methods exist for affinity selection of binding proteins or polypeptides such as phage display[5], yeast surface display[15], MRNA display[16] or peptide-on-bead display[17]. Herein, phage display using the fUSE5/6-mer library based on the filamentous phage vector fd-tet[18] was used to select short peptides which bind to the articular cartilage matrix. Embodiments of the invention include using affinity selection of binding proteins or peptides against cartilage ex vivo.

In this case, biopanning was carried out against slices of bovine cartilage. Conditions in the binding step were chosen with increasing stringency from round 1 to 5 in order to favor binding of high affinity polypeptides. The selected sequences obtained from DNA sequencing of 96 clones have been evaluated in a competetive binding assay. Two sequences C1-3 and C1-C1 exhibited stronger competetive binding than C1-F1 and random phages from the fUSE5 library (FIG. 1b). Therefore, specificity of binding for C1-3 and C1-C1 to cartilage was further assessed. The phage clones were subjected to physiological conditions (37° C. and shaking) and binding specificity probed for cartilage, cartilage in the presence of synovial fluid and the synovial membrane. Phage titers of both C1-3 and C1-C1 were higher for cartilage than for synovial membrane by two orders of magnitude. More importantly, binding to the cartilage target was not impaired by the addition of synovial fluid (FIG. 1c). This is likely to be the result of the negative screening which was carried out during the first round of biopanning. In order to eliminate phages with polypeptide sequences that potentially bind to constituents of the synovial fluid, the first screening was carried out in the presence of synovial fluid, which was discarded including the phages before the binding phages were eluted off the cartilage slice. In order assess the relative binding affinity of the polypeptide sequence, the corresponding polypeptide WYRGRLC (SEQ ID NO:4) was synthesized. In a competetive binding assay against the phage C1-3 displaying WYR-GRL (SEQ ID NO:1) ($10^8$ TU/ml) an IC50 in the high nanomolar range of about 200 nM can be demonstrated (FIG. 2).

Binding specificity was conferred by the polypeptide sequence rather than the net positive charge of the polypeptide which sticks non-specifically to negatively charged proteoglycans. This is demonstrated in FIG. 3 in that 10 µM of WYRGRLC (SEQ ID NO:4) resulted in a decrease of phage titers close to 100 fold. By contrast, 10 µM of YRLGRWC (SEQ ID NO:7), which comprises the same amino acids just in scrambled order, did not result in a significant decrease in phage titer as compared to control phage titers without polypeptide. Thus WYRGRLC (SEQ ID NO:4) is a short polypeptide with specific binding to articular cartilage which shows a dose dependent decrease in competetive binding against phage C1-3. The other polypeptides, DPHFHL (SEQ ID NO:2) and RVMLVR (SEQ ID NO:3), which were discovered using the same experimental methods used for WYRGRL, could also be shown to have specific binding using these same techniques.

The polypeptides were synthesized such that they contain a cysteine at the C-terminus. The free thiol of cysteine is used for bioconjugation by Michael-type addition to Pluronic-di-vinyl sulfone which serves as the emulsifier in nanoparticle synthesis and therefore remains displayed on the particle surface. While this is a straightforward scheme for surface functionalisation of nanoparticles synthesized by inverse emulsion polymerization, conjugation of Pluronic requires excess of polypeptide despite the favorable kinetics of Michael-type addition of free thiols to vinyl sulfone, if conjugation close to 100% is to be achieved as evidenced by $^1$H-NMR. In addition, some Pluronic is always lost during nanoparticle synthesis. Alternative synthetic schemes therefore add surface functionality to already-synthesized nanoparticles in order to limit the amount of polypeptide needed.

Presence of the polypeptide on the nanoparticle surface as indicated by a shift in zeta-potential from neutral to positive was confirmed by competetive binding. WYRGRLC(SEQ ID NO:4)-PPS nanoparticles with a degree of surface functionalisation of 10% (w/w of total Pluronic used) at a concentration of 2% (w/v) against phage clone C1-3 ($10^8$ TU/ml) to articular cartilage resulted in a similar decrease of phage titers as 10 µM of free polypeptide WYRGRLC (SEQ ID NO:4, FIG. 3).

Targeting the extra-cellular matrix of articular cartilage essentially depends on the ability of the drug delivery system to enter the cartilage matrix and to stay there. In passive targeting, the distribution of nanoparticles in the joint is mainly governed by the capability of tissue penetration and cellular uptake. While larger particles do not enter, smaller ones are able to penetrate and reside in the cartilage ECM. It is demonstrated in herein that nanoparticles (in this case, nanoparticles with a mean volume diameter of 36 and 38 nm) are able to enter the articular cartilage ECM and meniscal tissue in addition to the synovium. It is consistent with the literature that small particles possess the ability to enter the cartilage ECM. It has been demonstrated that adeno-associated viruses (AAV) with a mean diameter of 20-25 nm enter the articular cartilage matrix up to a depth of penetration of 450 µm in normal and 720 µm in degraded cartilage[19]. While both surface-functionalised and non-functionalised PPS nanoparticles enter the articular cartilage matrix, there is a marked increase in the accumulation of WYRGRLC (SEQ ID NO:4)-PPS nanoparticles over non-functionalised and therefore non-targeted PPS nanoparticles 24 hours after intra-articular injection into the knee joint of mice (FIG. 4). WYR-GRLC(SEQ ID NO:4)-PPS nanoparticles therefore exhibit specific targeting capability for the articular cartilage matrix. Although the basic research has been performed with bovine cartilage, the polypeptide sequences described herein are expected to bind to human articular cartilage due to the general homology of these tissues. Bovine cartilage is an accepted model in cartilage research due to the very limited availability of healthy human cartilage.

Polypeptide Ligands Specific for Articular Cartilage

Three of the cartilage tissue-binding ligands are polypeptides with the amino acid sequence of WYRGRL (SEQ ID NO:1), DPHFHL (SEQ ID NO:2), or RVMLVR (SEQ ID NO:3). Other ligands are polypeptides or functional polypeptides with sequences that have conservative substitutions of one of SEQ ID NOs. 1, 2, or 3.

Certain embodiments are directed to the subset of polypeptides that have a certain percentage identity to the disclosed sequences, or a certain degree of substitution, with the subset being primarily, or only, functional polypeptides.

The binding activity of a polypeptide to cartilage may be determined simply by following experimental protocols as described herein. For instance, a polypeptide variant of one of the polypeptide ligands may be labeled with a marker (e.g., radioactive or fluorescent) and exposed to bovine cartilage to determine its binding affinity using well-known procedures. A binding assay may be performed using a simple fluorescence readout using a plate reader by labeling polypeptide variants with a fluorescent marker, e.g., 6-fluorescein iodoacetamide which reacts with the free thiol of the cysteine. Using such a method, the binding strengths of polypeptide variants relative to e.g., WYRGRLC (SEQ ID NO:4) under given physiological conditions can be determined, e.g., sequences made using conservative substitutions, truncations of the sequences to 5 or less amino acids, addition of flanking groups, or changes or additions for adjusting sequences for solubility in aqueous solution.

Polypeptides of various lengths may be used as appropriate for the particular application. In general, polypeptides that contain the polypeptide ligand sequences will exhibit specific binding if the polypeptide is available for interaction with cartilage in vivo. Protein folding can affect the bioavailability of the polypeptide ligands. Accordingly, certain embodiments are directed to polypeptides that have a polypeptide ligand but do not occur in nature, and certain other embodiments are directed to polypeptides having particular lengths, e.g., from 6 to 3000 residues, or 6-1000, or 6-100, or 6-50; artisans will immediately appreciate that every value and range within the explicitly articulated limits is contemplated. Moreover, the lower limits may be 4 or 5 instead of 6.

While polypeptides of 6 residues were extensively, tested, variants that have 3, 4, or 5, residues can also be active and exhibit specific binding, as well as conservative substitutions thereof. Accordingly, every contiguous 3, 4, and 5 residues in each sequence can be rapidly screened and tested for binding using the methods set forth herein, e.g., using the sequencing and binding assays, or with competitive inhibition. Thus, in the case of SEQ ID NO:1, with W being the first residue and L the sixth residue, binding activity may be expected in the three residues 1-3, 2-4, 3-5, and 4-6; for four residues, binding activity may be expected in 1-4, 2-5, and 3-6; for five residues, binding activity may be expected in positions 1-5 or 2-6. The ordinary artisan, after reading this disclosure, will be able to quickly assay this limited number of sequences. While some decrease in binding activity might be observed when the 6-residue sequences are truncated, a core group is expected to exhibit substantial binding. This expectation is based on general observations made with binding moieties in these arts. For example, in phage display experiments, the peptide sequences often exhibit a consensus motif which usually does not involve all residues displayed on the phage virion, e.g., in Arap et al. (Nature Medicine 2002;8:121). Less stringent conditions or sequencing of previous rounds are more likely to give a consensus motif in different peptide sequences than one very strong binding sequence.

Certain embodiments provide various polypeptide sequences and/or purified polypeptides. A polypeptide refers to a chain of amino acid residues, regardless of post-translational modification (e.g., phosphorylation or glycosylation) and/or complexation with additional polypeptides, synthesis into multisubunit complexes, with nucleic acids and/or carbohydrates, or other molecules. Proteoglycans therefore also are referred to herein as polypeptides. As used herein, a "functional polypeptide" is a polypeptide that is capable of promoting the indicated function. Polypeptides can be produced by a number of methods, many of which are well known in the art. For example, polypeptides can be obtained by extraction from a natural source (e.g., from isolated cells, tissues or bodily fluids), by expression of a recombinant nucleic acid encoding the polypeptide, or by chemical synthesis. Polypeptides can be produced by, for example, recombinant technology, and expression vectors encoding the polypeptide introduced into host cells (e.g., by transformation or transfection) for expression of the encoded polypeptide.

There are a variety of conservative changes that can generally be made to an amino acid sequence without altering activity. These changes are termed conservative substitutions or mutations; that is, an amino acid belonging to a grouping of amino acids having a particular size or characteristic can be substituted for another amino acid. Substitutes for an amino acid sequence may be selected from other members of the class to which the amino acid belongs. For example, the nonpolar (hydrophobic) amino acids include alanine, leucine, isoleucine, valine, proline, phenylalanine, tryptophan, and tyrosine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Such alterations are not expected to substantially affect apparent molecular weight as determined by polyacrylamide gel electrophoresis or isoelectric point. Exemplary conservative substitutions include, but are not limited to, Lys for Arg and vice versa to maintain a positive charge; Glu for Asp and vice versa to maintain a negative charge; Ser for Thr so that a free —OH is maintained; and Gln for Asn to maintain a free $NH_2$. Moreover, point mutations, deletions, and insertions of the polypeptide sequences or corresponding nucleic acid sequences may in some cases be made without a loss of function of the polypeptide or nucleic acid fragment. Substitutions may include, e.g., 1, 2, 3, or more residues. The amino acid residues described herein employ either the single letter amino acid designator or the three-letter abbreviation. Abbreviations used herein are in keeping with the standard polypeptide nomenclature, J. Biol. Chem., (1969), 243, 3552-3559. All amino acid residue sequences are represented herein by formulae with left and right orientation in the conventional direction of amino-terminus to carboxy-terminus.

In some cases a determination of the percent identity of a peptide to a sequence set forth herein may be required. In such cases, the percent identity is measured in terms of the number of residues of the peptide, or a portion of the peptide. A polypeptide of, e.g., 90% identity, may also be a portion of a larger peptide Variations of the disclosed polypeptide sequences include polypeptides or functional polypeptides having about 83% identity (e.g., 1 of 6 substituted) or about 67% identity (e.g., 2 of 6 substituted).

The term purified as used herein with reference to a polypeptide refers to a polypeptide that either has no naturally occurring counterpart (e.g., a peptidomimetic), or has been chemically synthesized and is thus substantially uncontaminated by other polypeptides, or has been separated or purified from other most cellular components by which it is naturally accompanied (e.g., other cellular proteins, polynucleotides, or cellular components). An example of a purified polypeptide is one that is at least 70%, by dry weight, free from the proteins and naturally occurring organic molecules with which it naturally associates. A preparation of the a purified polypeptide therefore can be, for example, at least 80%, at least 90%, or at least 99%, by dry weight, the polypeptide. Polypeptides also can be engineered to contain a tag sequence (e.g., a polyhistidine tag, a myc tag, or a Flag® tag) that facilitates the polypeptide to be purified or marked (e.g., captured onto an affinity matrix, visualized under a microscope). Thus a purified composition that comprises a polypeptide refers to a purified polypeptide unless otherwise indicated.

Polypeptides may include a chemical modification; a term that, in this context, refers to a change in the naturally-occurring chemical structure of amino acids. Such modifications may be made to a side chain or a terminus, e.g., changing the amino-terminus or carboxyl terminus. In some embodiments, the modifications are useful for creating chemical groups that may conveniently be used to link the polypeptides to other materials, or to attach a therapeutic agent.

Nanoparticles

As demonstrated by the foregoing examples, the cartilage tissue-binding ligands may be used to target nanoparticles to a cartilage tissue, and such nanoparticles may include a therapeutic agent, for example, one or more of the therapeutic agents described herein. While certain polymer-therapeutics have been described elsewhere, these have mainly been designed to augment drug concentrations in tumor tissues[1]. Such alteration of the biodistribution of anticancer drugs through delivery systems aims at reducing the drug's toxicity and at improving therapeutic effects[2,3]. To be effective, a drug delivery system must escape non-specific systemic accumulation and phagocytotic clearance by the host defense immune system. Moreover, after accumulation at the target site, penetration of the often avascular tissue must be achieved and the drugs released in active forms in order to exert the therapeutic effect. For targeting articular cartilage, non-specific systemic accumulation can be avoided by direct intra-articular injection. While this is an attractive treatment approach because it minimizes systemic effects, small compounds are prone to rapid lymphatic clearance and possess a residence time of as short as 1-5 hours[4].

In order to minimize intra-articular injections and to increase the bioavailability of drugs in articular cartilage, the nanoparticle-based therapeutic agent delivery system described herein exhibits active targeting functionality for the cartilage, specifically, cartilage extra-cellular matrix. The combination of targeting functionality and a nanoparticle-based delivery system enables better control of bioavailability and biodistribution, particularly for intra-articular drug delivery to the cartilage matrix. Surface functionalisation of nanoparticles with the selected peptides controls the biodistribution by specific accumulation of nanoparticles in the articular cartilage, specifically in the extra-cellular matrix. The cartilage matrix itself therefore serves as a reservoir of nanoparticle encapsulated therapeutic molecules, which are delivered to the site of the disease process.

As explained herein, articular cartilage can be targeted in vivo with nanoparticles by the use of polypeptides which have been characterized to exhibit specific homing activity to articular cartilage. While PPS nanoparticles are used herein for demonstrative purposes, other techniques for making nanoparticles may also be adapted. As exemplified with the inverse emulsion polymerisation technique for PPS nanoparticle preparation by which the emulsifier remains displayed on the surface[14], the targeting polypeptides were made bioavailable by exposure at a surface of the nanoparticles. Size control was achieved in this particular technique by adjusting the emulsifier to monomer ratio and yielded sizes ranging from about 20 nm to about 200 nm[14]. While the density of the cartilage extra-cellular matrix represents a relevant obstacle not just for the screening of combinatorial peptide libraries but potentially also for drug delivery to the cartilage, the use of suitably-sized nanoparticles and/or ligands with specific binding to the cartilage enchances delivery efficiency.

Nanoparticles are be prepared as collections of particles having an average diameter of between about 10 nm and about 200 nm, including all ranges and values between the explicitly articulated bounds, e.g., from about 20 to about 200, and from about 20 to about 40, to about 70, or to about 100 nm, depending on the polydispersity which is yielded by the preparative method. Detailed methods for making and delivering nanoparticles are set forth below and in U.S. Pat. Ser. No. 60/775,132, filed Feb. 21, 2006, which is hereby incorporated by reference herein. Numerous nanoparticle systems can be utilized, such as those formed from copolymers of poly(ethylene glycol) and poly(lactic acid), those formed from copolymers of poly(ethylene oxide) and poly (beta-amino ester), and those formed from proteins such as serum albumin. Other nanoparticle systems are known to those skilled in these arts. See also Devalapally et al., *Cancer Chemother Pharmacol.*, 07-25-06; Langer et al., *International Journal of Pharmaceutics*, 257:169-180 (2003); and Tobio et al., *Pharmaceutical Research*, 15(2):270-275 (1998).

Larger particles of more than about 200 nm average diameter incorporating the cartilage tissue-binding ligands may also be prepared, with these particles being termed microparticles herein since they begin to approach the micron scale and fall approximately within the limit of optical resolution. For instance, certain techniques for making microparticles are set forth in U.S. Pat Nos. 5,227,165, 6,022,564, 6,090, 925, and 6,224,794.

Functionalization of nanoparticles to employ targeting capability requires association of the targeting polypeptide with the particle, e.g., by covalent binding using a bioconjugation technique, with choice of a particular technique being guided by the particle or nanoparticle, or other construct, that the polypeptide is to be joined to. In general, many bioconjugation techniques for attaching peptides to other materials are well known and the most suitable technique may be chosen for a particular material. For instance, additional amino acids may be attached to the polypeptide sequences, such as a cysteine in the case of attaching the polypeptide to thiol-reactive molecules. Herein is described an example of conjugation of the polypeptide WYRGRL (SEQ ID NO:1) with a cysteine at the C-terminus to Pluronic-F127 which was derivatized with thiol-reactive vinyl sulfone. The polypeptide was covalently bound to Pluronic by Michael-type addition and can subsequently be used for nanoparticle synthesis.

Proteins Targeted to Articular Cartilage Tissue

Therapeutic agents such as therapeutic polypeptides can be furnished with targeting capability by the use of the polypeptide ligands described and advantageously exhibit longer retention times in a joint, for instance by making a fusion protein of a polypeptide ligand and a therapeutic protein. By designing gene specific primers for the therapeutic polypeptide to be expressed, the polypeptide ligands can be attached to the N- or C-terminus in normal or reverse order. One of the primers, forward or reverse depending whether the polypeptide ligand is supposed to be localized at the N- or C-terminus, contains a gene sequence of the appropriate therapeutic polypeptide. For example, to make a fusion protein of a given therapeutic polypeptide and (GGG)WYRGRL (SEQ ID NO:8) ligand at the C-terminus, the reverse primer corresponds to 5'-ctgatgcggccgctcTCACAGCCTGC-CCCTATACCAGCCGCCGCCxxxxx-3' (SEQ ID NO:9) which contains the codon sequence for WYRGRL in reverse complement with a N-terminal glycine (GGG) linker (capital letters), as well as a stop codon and a restriction site for NotI and an overhang. The Xs correspond to the therapeutic polypeptide specific sequence and may be, e.g., around 20 base pairs long, although other lengths may be used as per conventional practice in these arts. The same example with same restriction site for a N-terminal localization of WYR-GRL(GGG) (SEQ ID NO:10) corresponds to 5'-atcaggagcggccgcTGGTATAGGGGCAGGCTGGGCGGCGGCxxxxx-3' (SEQ ID NO:11) or conservative substitutions of the codon sequence. Instead of the three glycines as a linker, other linkers appropriate to the properties of the therapeutic polypeptides can be chosen. Similarly, other target ligands may be encoded, e.g., using thea nucleic acid sequence 5'-ctgatgcggccgctcAAGATGGAAATGAG-GATCGCCGCCGCCxxxxx-3' (SEQ ID NO: 12) that endocdes DPHFHLGGG (SEQ ID NO:13) or the nucleic acid 5'-ctgatgcggccgctcACGAACAAGCAT-AACACGGCCGCCGCCxxxxx-3' (SEQ ID NO:14) that encodes RVMLVRGGG (SEQ ID NO:15). Thus a DNA sequence for WYRGRL (SEQ ID NO:1) is TGGTAT-AGGGGCAGGCTG (SEQ ID NO:16), and for DPHFHL (SEQ ID NO:2) is AAGATGGAAATGAGGATC (SEQ ID NO:17), and for RVMLVR (SEQ ID NO:3) is ACGAA-CAAGCATAACACG (SEQ ID NO:18).

Certain therapeutic polypeptides include proteins present in cartilage, e.g., tissue inhibitors of matrix metalloproteinase-3 (TIMP-3), growth factors (e.g., Transforming growth factor-beta (TGF-β), growth developmental factor-5 (GDF-5), CYR61 (Cystein-rich61)/CTGF (connective tissue growth factor)/NOV (Nephroblastoma overexpressed) (CCN2), insulin-like growth factor-1 (IGF-1), and bone morphogenic proteins (BMPs). Certain embodiments are molecules for viscosupplementation, e.g., molecules found in human cartilage that include chondroitin sulfate, keratane sulfate, hyaluronic acid, proteoglycans.

In some embodiments, a fusion protein is prepared and introduced into the body as a purified composition in a pharmaceutically acceptable condition, or with a pharmaceutical excipient. In certain embodiments, the fusion protein is produced using a cell, either a procaryotic or a eucaryotic cell. In other embodiments, nucleic acids encoding a fusion protein are introduced into a patient, in which case the nucleic acids may be "naked" or part of a larger construct, e.g., a vector. In other embodiments, transfected cells are introduced into a patient. The site of introduction may be, e.g., systemic, in a joint, or in a cartilage tissue.

Cartilage Binding Fusion Protein: Targeted Recombinant TIMP-3

Tissue inhibitor of matrix metalloproteinase 3 (TIMP-3) is a relatively insoluble matricellular protein[30] which inhibits several matrix metalloproteinases (MMP-1, -2, -9)[31] in addition to aggrecanase 1 and 2, i.e. ADAMTS4 and ADAMTS5[32]. As such, this molecule is beneficial in the treatment of osteoarthritis in any joint, specifically in a setting where the initiating mechanical cause is surgically corrected. Because TIMP-3 blocks these matrix degradative enzymes, the equilibrium in matrix turn-over of articular cartilage may be restored by preventing further degradation. TIMP-3 is not specifically expressed in articular cartilage, however, and due to its ability of inhibiting several enzymes may have severe potential adverse effects upon systemic administration or systemic dissemination following intra-articular injection. Targeted delivery of the inhibitory domain of TIMP-3 to articular cartilage can prevent potential systemic dissemination while increasing the therapeutic effect of the molecule in the cartilage matrix, i.e. at the site of the disease process in osteoarthritis. Moreover, the inhibitory domain of TIMP-3 also serves as a protectant against cartilage degradation in conditions such as rheumatoid arthritis, bacterial arthritis or reactive arthritis. Disclosed herein is a targeted recombinant TIMP-3 (trTIMP-3) (fusion protein which contains one of the sequences (SEQ ID NO:1, SEQ ID NO:2, SEQ ID NO:3) or conservative subsitutions thereof, e.g., at the N- or C-terminus. While TIMP-3 has been selected as an embodiment, other protease inhibitors or matrix metalloproteinase inhibitors may also be made and used by following the general procedures disclosed herein.

TIMP-3 contains a signal domain, residues 1 to 24, the N-terminal inhibitory domain, residues 24 to 143, and an extra-cellular matrix binding domain, residues 143 to 211 (SwissProt entry P35625). It has been demonstrated that N-TIMP-3, i.e. residues 24 to 143, is sufficient for exhibiting inhibitory activities on ADAMTS4 and ADAMTS5 as well as MMP-1 and MMP-2[3]. Accordingly, it is possible to engineer a fusion protein of N-TIMP-3 (Cys24 to Asn 143) which contains the sequence WYRGRL (SEQ ID NO:1) at the C-terminus. The natural non-specific C-terminal extra-cellular matrix binding domain is substituted with a targeting polypeptide specific for articular cartilage.

Human (P35625) and mouse N-TIMP-3 (P39876) share 97% sequence homology differing in three amino acid residues. Two of these residues represent conservative substitutions, Thr vs. Ser at residue 74 and Asp vs. Glu at residue 110. At residue 126 His substituted for Gln, which lies in a domain linking two α-chains.

For cloning, the sequence in NM_000362 was used for primer design. The primers were designed as explained above (see SEQ ID NO:9 for reversed primer and SEQ ID NO:11 for the forward primer). RNA was isolated using a RNeasy MinElute spin column (Qiagen, Hombrechikon, Switzerland) from immature murine articular chondrocytes which have been isolated from epiphyseal cartilage of neonatal mice using a two step digestion protocol with collagenase D (Roche, Basel, Switzerland). First-strand cDNA was generated using SuperScript III (Invitrogen, Carlsbad, Calif.) with an Oligo-dT(20) primer (Microsynth, Balgach, Switzerland). RT-PCR for amplifying the required DNA fragments was carried out with a proof-reading DNA polymerase (Pfu Turbo polymerase, Stratagene, LaJolla, Calif.) and the fragments with a required length of 420 bp checked by agarose-gel electrophoresis. The DNA fragments were gel purified with a Nucleospin II column (Macherey-Nagel, Düren, Germany), cut with the corresponding restriction enzymes BamHI and NotI (New England BioLabs Inc., Ipswich, Mass.) and ligated into the bacterial protein expression vector pGEX-4T-1 (Amersham Biosciences, GE Healthcare Europe, Otelfingen, Switzerland), which expresses trTIMP-3 as a fusion protein with glutathione-S-transferase (GST) for purification, total MW 40 kDa. For bacterial expression, E. coli strain BL21 was transformed with the trTIMP-3-pGEX construct by electroporation. An optimal expression clone was selected by anti-GST ELISA.

Bacterial cultures were grown in 2xYT until they reached an $A_{600}$ of 0.6 to 0.7. Protein expression was then induced by 0.5M IPTG for 3 hours. To collect the protein from inclusion bodies, the bacteria were centrifuged, lysed by sonication and centrifuged again. The pellet was resuspended in a denaturing buffer (0.1M Tris-HCl, 50 mM glycine, 8 mM β-mercaptoethanol, 8M urea, 0.2M PMSF, pH 8.0) and stirred overnight, centrifuged for 20 min. at 48000xg and the supernatant collected for refolding. Refolding was performed by dialysing (24 kDa MWCO) the supernatant against a large volume of refolding buffer at 4° C. with decreasing amounts of urea to slowly remove the denturing agent (0.1M Tris-HCl, 1 mM EDTA, 0.2 mM PMSF, pH 8.0 supplemented with 4M, 2M, 1M and 0M urea each for 24 hrs). The last step of dialysis was carried out against PBS for 24 hours. The refolded protein was freed from precipitations by centrifugation and subsequently purified by FPLC with a GST binding column (GSTrap FF, Amersham Biosciences, GE Healthcare Europe, Otelfingen, Switzerland). The GST tag of purified trTIMP-3-GST fusion protein was cleaved of by incubation with thrombin for 24 hours and purified by FPLC from GST with the GSTrap FF column and from thrombin with a HiTrap Benzamidine FF column (Amersham Biosciences, GE Healthcare Europe, Otelfingen, Switzerland). Overall yield of trTIMP-3 was about 1.5 mg/l of bacterial culture.

The activity of purified trTIMP-3 was assessed by MMP-2 zymography in which an equimolar amount of trTIMP-3 completely inhibits MMP-2 activity indicating a nearly 100% activity of the purified protein. Further experiments could be used to demonstrate the aggrecanase inhibiting activity of trTIMP-3 and the targeting specificity to articular cartilage in a similar fashion as shown for the nanoparticles described herein. In addition, its therapeutic potential to prevent cartilage degradation could be demonstrated in a suitable animal model, e.g., in a mouse knee instability model.

Vectors

Accordingly, certain embodiments are directed to vectors for expression of a therapeutic protein of interest, e.g., a therapeutic agent and a polypeptide ligand. Nucleic acids encoding a polypeptide can be incorporated into vectors. As used herein, a vector is a replicon, such as a plasmid, phage, or cosmid, into which another nucleic acid segment may be inserted so as to bring about replication of the inserted segment. Vectors of the invention typically are expression vectors containing an inserted nucleic acid segment that is operably linked to expression control sequences. An expression vector is a vector that includes one or more expression control sequences, and an expression control sequence is a DNA sequence that controls and regulates the transcription and/or translation of another DNA sequence. Expression control sequences include, for example, promoter sequences, transcriptional enhancer elements, and any other nucleic acid elements required for RNA polymerase binding, initiation, or termination of transcription. With respect to expression control sequences, "operably linked" means that the expression control sequence and the inserted nucleic acid sequence of interest are positioned such that the inserted sequence is transcribed (e.g., when the vector is introduced into a host cell). For example, a DNA sequence is operably linked to an expression-control sequence, such as a promoter when the expression control sequence controls and regulates the transcription and translation of that DNA sequence. The term "operably linked" includes having an appropriate start signal (e.g., ATG) in front of the DNA sequence to be expressed and maintaining the correct reading frame to permit expression of the DNA sequence under the control of the expression control sequence to yield production of the desired protein product. Examples of vectors include: plasmids, adenovirus, Adeno-Associated Virus (AAV), Lentivirus (FIV), Retrovirus (Mo-MLV), and transposons. There are a variety of promoters that could be used including, but not limited to, constitutive promoters, tissue-specific promoters, inducible promoters, and the like. Promoters are regulatory signals that bind RNA polymerase in a cell to initiate transcription of a downstream (3' direction) coding sequence.

Targeted Delivery of Viscosupplementation

Molecules for viscosupplementation may be conjugated with polypeptide ligands described herein to form a conjugate for enhanced delivery and effect in the cartilage. The formation of such conjugates is within the skill of ordinary artisans and various techniques are known for accomplishing the conjugation, with the choice of the particular technique being guided by the materials to be conjugated. Such conjugates may be delivered systemically or locally, e.g., orally or by injection to a joint. Thus hyaluronic acid conjugation with a polypeptide ligand disclosed herein may prolong the retention time of hyaluronic acid in the joint and therefore enhance the efficacy of intra-articular viscosupplementation with hyaluronic acid. Conjugation of the polypeptide to hyaluronic acid can be performed either directly as described above, or by the use of a polymer linker. Examples of polymer linkers are biocompatible hydrophilic polymers, including polymers free of amino-acids. For instance, a polymer linker may be a polyethylene glycol (PEG). Hyaluronic acid can be functionalized with acrylated PEG-Arg-Gly-Asp conjugates created by Michael-type addition chemistry (Park et al. Biomaterials 2003;24:893-900). In general, polymers described herein for use with the polypeptide ligands may be free of amino acids, meaning that such polymers do not contain a natrual or synthetic amino acid.

In some embodiments, the conjugate is prepared and introduced into the body as a purified composition in a pharmaceutically acceptable condition, or with a pharmaceutical excipient. In certain embodiments, the conjugate is produced using a cell, either a procaryotic or a eucaryotic cell, as in the case of a biopolymer. In other embodiments, transfected cells are introduced into a patient. The site of introduction may be, e.g., systemic, in a joint, or in a cartilage tissue.

Targeting Genes Condensed with Polymers with the Polypeptides Attached

A small gene delivery system will have advantages with respect to penetrating the dense matrix of cartilage tissue. In some embodiments, therefore, the delivery system uses significantly condensed DNA, to enter the cartilage matrix and transfect non-dividing quiescent chondrocytes or other cells. In some embodiments, therefore, polypeptide ligands are attached to polymers which contain a nuclear localisation sequence to form a conjugate and are used to condense DNA to overcome challenges to gene transfection in chondrocytes embedded in the cartilage matrix. Some aspects of these techniques have been described by in Trentin et al. PNAS 2006;103:2506-11 and J Control Release 2005;102:263-75. Thus in certain embodiments the conjugate associated with nucleic acids encoding a therapeutic polypeptide is prepared and introduced into the body as a purified composition in a pharmaceutically acceptable condition, or with a pharmaceutical excipient. In certain embodiments, such a conjugate is produced using a cell, either a procaryotic or a eucaryotic cell, as in the case of a biopolymer. In other embodiments, transfected cells are introduced into a patient. The site of introduction may be, e.g., systemic, in a joint, or in a cartilage tissue.

Therapeutic Agents Associated with Ligands for Delivery to Cartilage

Polypeptides as described herein can be attached to other polymers through bioconjugation. The formation of such conjugates is within the skill of ordinary artisans and various techniques are known for accomplishing the conjugation, with the choice of the particular technique being guided by the materials to be conjugated. The addition of amino acids to the polypeptide (C- or N-terminal) which contain ionizable side chains, i.e. aspartic acid, glutamic acid, lysine, arginine, cysteine, histidine, or tyrosine, and are not contained in the active portion of the polypeptide sequence, serve in their unprotonated state as a potent nucleophile to engage in various bioconjugation reactions with reactive groups attached to polymers, i.e. homo- or hetero-bi-functional PEG (e.g., Lutolf and Hubbell, Biomacromolecules 2003;4:713-22, Hermanson. Bioconjugate Techniques. London. Academic Press Ltd; 1996). An application where this may be useful is again for targeted delivery of a therapeutic agent. In some embodiments, the agent is attached to a soluble polymer, and may be adminsited to a patient in a pharmaceutically acceptable form. Or a drug may be encapsulated in polymerosomes or vesicles or covalently attached to polymers. In the latter case, drugs are attached to the polymer backbone with a degradable site-specific spacer or linker (Lu et al. J Control Release 2002;78:165-73).

In general, soluble hydrophilic biocompatbile polymers may be used to ensure that the conjugate is soluble and will be bioavailable after introduction into the patient. Examples of soluble polymers are polyvinyl alcohols, polyethyleene imines, and polyethylene glycols (a term including polyethylene oxides) having a molecular weight of at least 100, 400, or between 100 and 400,000 (with all ranges and values between these explicit values being contemplated). Solubility refers to a solubility in water or physiological saline of at least 1 gram per liter. Domains of biodegradable polymers may also be used, e.g., polylactic acid, polyglycolic acid, copolymers of polylactic and polyglycolic acid, polycaprolactones, polyhydroxy butyric acid, polyorthoesters, polyacetals, polydihydropyrans, and polycyanoacylates.

In some embodiments, a polypeptide-polymer association, e.g., a conjugate, is prepared and introduced into the body as a purified composition in a pharmaceutically acceptable condition, or with a pharmaceutical excipient. The site of introduction may be, e.g., systemic, in a joint, or in a cartilage tissue.

Cartilage Defect Treatment Using Polypeptide Ligands with Specific Binding for Cartilage The polypeptides ligands were discovered based on their binding affinity for the cartilage matrix but are not specifically bound to the articular surface. Therefore, besides embodiments such as targeting the cartilage matrix by therapeutic agent delivery systems or with engineered fusion proteins, the polypeptides are particularly well suited to target a defect because extracellular matrix is exposed at the defect. This feature is useful for delivering biomaterials for gene, protein and/or cell delivery to mediate cartilage defect repair. Accordingly, embodiments include treating a defect in an articular cartilage using one of the embodiments set forth herein. In fact, giving a biomaterial the capability of adhering or otherwise specifically binding to a cartilage defect does not only allow for injectable defect repair strategies but also may enhance retention of the biomaterial in the cartilage defect. A variety of chemical schemes can be used to incorporate the cartilage-binding polypeptide into the biomaterial. For example, using a material as described by Sawhney et al., a chemical approach for incorporation as described by Hern et al. can be employed (Sawhney et al. Macromolecules 1993; 26:581-587 and Hern et al. J. Biomed. Mater. Res. 1998; 39:266-276). As another example, using a material as described by Lutolf et al., a chemical approach for incorporation as described therein can be employed (Lutolf et al. Nature Biotechnol. 2003; 21:513-518). In general, the modification of such biomaterials is within the skill of ordinary artisans and various techniques are known for accomplishing the modification, with the choice of a particular technique being guided by the biomaterial and peptides to be conjugated.

Specific binding, as that term is commonly used in the biological arts, generally refers to a molecule that binds to a target with a relatively high affinity compared to non-target tissues, and generally involves a plurality of non-covalent interactions, such as electrostatic interactions, van der Waals interactions, hydrogen bonding, and the like. Specific binding interactions characterize antibody-antigen binding, enzyme-substrate binding, and specifically binding protein-receptor interactions; while such molecules may bind tissues besides their targets from time to time, such binding is said to lack specificity and is not specific binding. The peptides of SEQ ID NOs 1, 2, and 3 may bind non-cartilage tissues in some circumstances but such binding has been observed to be non-specific, as evidenced by the much greater binding of the peptides to the targeted tissue as opposed to surrounding joint tissues (data not shown).

Accordingly, embodiments include biomaterials comprising at least one of the ligands disclosed herein that are used to fill or augment a defect in a cartilage. A defect refers to a void in a surface (e.g., a pit, tear, or hole) or a pathological discontinuity in a surface (e.g., a tear or eroded member). Fill refers to essentially filling or covering the defect or bridging the discontinuity. Augment refers to at least partial filling. In some embodiments, the biomaterial is a solid prior to placement in a patient, while in other embodiments the material is made is situ, meaning it is formed from precursors at the site of the defect. Thus biomaterials for cartilage defects may be supplemented with a ligand or other embodiment set forth herein. Examples of such biomaterials include U.S. Pat. Nos. 5,874,500, and 5,410,016, and which include materials formed by in-situ polymerization. Biomaterials for targeting cartilage defects, i.e. adhering to a cartilage defect, are suited for the delivery of therapeutic agents to mediate cartilage repair such as growth factors and for cell delivery to the repair site. In accordance with techniques for autologuous cartilage transplantation/implantation the use of a biomaterial for cell delivery which adheres to the defect by the use of polypeptide ligands (SEQ ID NO:1 through 3) and acts as a morphogenic guide may improve carrtilage defect repair.

Nucleic Acids

Certain embodiments are directed to nucleic acids. As used herein, the term nucleic acid refers to both RNA and DNA, including siRNA, shRNA, miRNA, cDNA, genomic DNA, synthetic (e.g., chemically synthesized) DNA, as well as naturally occurring and chemically modified nucleic acids, e.g., synthetic bases or alternative backbones. A nucleic acid molecule can be double-stranded or single-stranded (i.e., a sense or an antisense single strand). An isolated nucleic acid refers to a nucleic acid that is separated from other nucleic acid bases that are present in a genome, including nucleic acids that normally flank one or both sides of a nucleic acid sequence in a vertebrate genome (e.g., nucleic acids that flank a gene). A conservatively substituted nucleic acid refers to the substitution of a nucleic acid codon with another codon that encodes the same amino acid and also refers to nucleic acids that encode conservatively substituted amino acids, as described herein with respect to polypeptides. Significantly, the combination of potential codons for a polypeptide of only about six residues is manageably small.

The nucleic acid sequences set forth herein are intended to represent both DNA and RNA sequences, according to the conventional practice of allowing the abbreviation "T" stand for "T" or for "U", as the case may be, for DNA or RNA. Polynucleotides are nucleic acid molecules of at least three nucleotide subunits. Polynucleotide analogues or polynucleic acids are chemically modified polynucleotides or polynucleic acids. In some embodiments, polynucleotide analogues can be generated by replacing portions of the sugar-phosphate backbone of a polynucleotide with alternative functional groups. Morpholino-modified polynucleotides, referred to herein as "morpholinos," are polynucleotide analogues in which the bases are linked by a morpholino-phosphorodiamidate backbone (see, e.g., U.S. Pat. Nos. 5,142,047 and 5,185,444). In addition to morpholinos, other examples of polynucleotide analogues include analogues in which the bases are linked by a polyvinyl backbone, peptide nucleic acids (PNAs) in which the bases are linked by amide bonds formed by pseudopeptide 2-aminoethyl-glycine groups, analogues in which the nucleoside subunits are linked by methylphosphonate groups, analogues in which the phosphate residues linking nucleoside subunits are replaced by phosphoroamidate groups, and phosphorothioated DNAs, analogues containing sugar moieties that have 2' O-methyl group). Polynucleotides of the invention can be produced through the well-known and routinely used technique of solid phase synthesis. Alternatively, other suitable methods for such synthesis can be used (e.g., common molecular cloning and chemical nucleic acid synthesis techniques). Similar techniques also can be used to prepare polynucleotide analogues such as morpholinos or phosphorothioate derivatives. In addition, polynucleotides and polynucleotide analogues can be obtained commercially. For oligonucleotides, examples of pharmaceutically acceptable compositions are salts that include, e.g., (a) salts formed with cations such as sodium, potassium, ammonium, etc.; (b) acid addition salts formed with inorganic acids, for example, hydrochloric acid, hydrobromic acid (c) salts formed with organic acids e.g., for example, acetic acid, oxalic acid, tartaric acid; and (d) salts formed from elemental anions e.g., chlorine, bromine, and iodine.

Pharmaceutical Carriers

Pharmaceutically acceptable carriers or excipient may be used to deliver embodiments as described herein. Excipient refers to an inert substance used as a diluent or vehicle for a therapeutic agent. Pharmaceutically acceptable carriers are used, in general, with a compound so as to make the compound useful for a therapy or as a product. In general, for any substance, a pharmaceutically acceptable carrier is a material that is combined with the substance for delivery to an animal. Conventional pharmaceutical carriers, aqueous, powder or oily bases, thickeners and the like may be necessary or desirable. In some cases the carrier is essential for delivery, e.g., to solubilize an insoluble compound for liquid delivery; a buffer for control of the pH of the substance to preserve its activity; or a diluent to prevent loss of the substance in the storage vessel. In other cases, however, the carrier is for convenience, e.g., a liquid for more convenient administration. Pharmaceutically acceptable salts of the compounds described herein may be synthesized according to methods known to those skilled in this arts. Thus a pharmaceutically acceptable composition has a carrier, salt, or excipient suited to administration to a patient. Moreover, inert components of such compositions are biocompatible and not toxic.

The compounds described herein are typically to be administered in admixture with suitable pharmaceutical diluents, excipients, extenders, or carriers (termed herein as a pharmaceutically acceptable carrier, or a carrier) suitably selected with respect to the intended form of administration and as consistent with conventional pharmaceutical practices. Thus the deliverable compound may be made in a form suitable for oral, rectal, topical, intravenous injection, intra-articular injection, or parenteral administration. Carriers include solids or liquids, and the type of carrier is chosen based on the type of administration being used. Suitable binders, lubricants, disintegrating agents, coloring agents, flavoring agents, flow-inducing agents, and melting agents may be included as carriers, e.g., for pills. For instance, an active component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like. The compounds can be administered orally in solid dosage forms, such as capsules, tablets, and powders, or in liquid dosage forms, such as elixirs, syrups, and suspensions. The active compounds can also be administered parentally, in sterile liquid dosage forms. Buffers for achieving a physiological pH or osmolarity may also be used.

All patent applications, patents, and publications mentioned herein are hereby incorporated by reference herein to the extent they do not directly contradict the explicit disclosures set forth herein.

REFERENCES

1. Duncan R. The dawning era of polymer therapeutics. *Nat Rev Drug Discov* 2003;2-5:347-60.
2. Bae Y, Nishiyama N, Fukushima S, Koyama H, Yasuhiro M, Kataoka K. Preparation and biological characterization of polymeric micelle drug carriers with intracellular pH-triggered drug release property: tumor permeability, controlled subcellular drug distribution, and enhanced in vivo antitumor efficacy. *Bioconjug Chem* 2005;16-1:122-30.
3. Nishiyama N, Okazaki S, Cabral H, Miyamoto M, Kato Y, Sugiyama Y, Nishio K, Matsumura Y, Kataoka K. Novel cisplatin-incorporated polymeric micelles can eradicate solid tumors in mice. *Cancer Res* 2003;63-24:8977-83.
4. Owen S G, Francis H W, Roberts M S. Disappearance kinetics of solutes from synovial fluid after intra-articular injection. *Br J Clin Pharmacol* 1994;38-4:349-55.
5. Smith G P, Petrenko V A. Phage Display. *Chem Rev* 1997; 97-2:391-410.
6. Kay B K, Kasanov J, Yamabhai M. Screening phage-displayed combinatorial peptide libraries. *Methods* 2001; 24-3:240-6.
7. Arap W, Kolonin M G, Trepel M, Lahdenranta J, Cardo-Vila M, Giordano R J, Mintz P J, Ardelt P U, Yao V J, Vidal C I, Chen L, Flamm A, Valtanen H, Weavind L M, Hicks M E, Pollock R E, Botz G H, Bucana C D, Koivunen E, Cahill D, Troncoso P, Baggerly K A, Pentz R D, Do K A, Logothetis C J, Pasqualini R. Steps toward mapping the human vasculature by phage display. *Nat Med* 2002;8-2:121-7.
8. Kolonin M G, Sun J, Do K A, Vidal C I, Ji Y, Baggerly K A, Pasqualini R, Arap W. Synchronous selection of homing peptides for multiple tissues by in vivo phage display. *Faseb J* 2006;20-7:979-81.
9. Pasqualini R, Ruoslahti E. Organ targeting in vivo using phage display peptide libraries. *Nature* 1996;380-6572: 364-6.
10. Kolonin M G, Saha P K, Chan L, Pasqualini R, Arap W. Reversal of obesity by targeted ablation of adipose tissue. *Nat Med* 2004; 10-6:625-32.
11. Lee L, Buckley C, Blades M C, Panayi G, George A J, Pitzalis C. Identification of synovium-specific homing peptides by in vivo phage display selection. *Arthritis Rheum* 2002;46-8:2109-20.
12. Comper W D. Physicochemical aspects of cartilage extracellular matrix. In: Hall B, Newman S, eds. *Cartilage: Molecular Aspects*. Boston: CRC Press, 1991:59-96.
13. Torzilli P A, Arduino J M, Gregory J D, Bansal M. Effect of proteoglycan removal on solute mobility in articular cartilage. *J Biomech* 1997;30-9:895-902.
14. Rehor A, Hubbell J A, Tirelli N. Oxidation-sensitive polymeric nanoparticles. *Langmuir* 2005;21-1:411-7.

15. Boder E T, Wittrup K D. Yeast surface display for screening combinatorial polypeptide libraries. *Nat Biotechnol* 1997;15-6:553-7.
16. Xu L, Aha P, Gu K, Kuimelis R G, Kurz M, Lam T, Lim A C, Liu H, Lohse P A, Sun L, Weng S, Wagner R W, Lipovsek D. Directed evolution of high-affinity antibody mimics using mRNA display. *Chem Biol* 2002;9-8:933-42.
Lam K S, Lebl M, Krchnak V. The "One-Bead-One-Compound" Combinatorial Library Method. *Chem Rev* 1997; 97-2:411-48.
18. Zacher A N, 3rd, Stock C A, Golden J W, 2nd, Smith G P. A new filamentous phage cloning vector: fd-tet. *Gene* 1980;9-1-2:127-40.
19. Madry H, Cucchiarini M, Terwilliger E F, Trippel S B. Recombinant adeno-associated virus vectors efficiently and persistently transduce chondrocytes in normal and osteoarthritic human articular cartilage. *Hum Gene Ther* 2003;14-4:393-402.
20. Phillips N C, Thomas D P, Knight C G, Dingle J T. Liposome-incorporated corticosteroids. II. Therapeutic activity in experimental arthritis. *Ann Rheum Dis* 1979;38-6:553-7.
21. Shaw I H, Knight C G, Thomas D P, Phillips N C, Dingle J T. Liposome-incorporated corticosteroids: I. The interaction of liposomal cortisol palmitate with inflammatory synovial membrane. *Br J Exp Pathol* 1979;60-2:142-50.
22. Ratcliffe J H, Hunneyball I M, Smith A, Wilson C G, Davis S S. Preparation and evaluation of biodegradable polymeric systems for the intra-articular delivery of drugs. *J Pharm Pharmacol* 1984;36-7:431-6.
23. Ratcliffe J H, Hunneyball I M, Wilson C G, Smith A, Davis S S. Albumin microspheres for intra-articular drug delivery: investigation of their retention in normal and arthritic knee joints of rabbits. *J Pharm Pharmacol* 1987; 39-4:290-5.
24. Tuncay M, Calis S, Kas H S, Ercan M T, Peksoy I, Hincal A A. In vitro and in vivo evaluation of diclofenac sodium loaded albumin microspheres. *J Microencapsul* 2000;17-2:145-55.
25. Horisawa E, Hirota T, Kawazoe S, Yamada J, Yamamoto H, Takeuchi H, Kawashima Y. Prolonged anti-inflammatory action of DL-lactide/glycolide copolymer nanospheres containing betamethasone sodium phosphate for an intra-articular delivery system in antigen-induced arthritic rabbit. *Pharm Res* 2002;19-4:403-10.
26. Horisawa E, Kubota K, Tuboi I, Sato K, Yamamoto H, Takeuchi H, Kawashima Y. Size-dependency of DL-lactide/glycolide copolymer particulates for intra-articular delivery system on phagocytosis in rat synovium. *Pharm Res* 2002;19-2:132-9.
27. Quinn T M, Morel V, Meister J J. Static compression of articular cartilage can reduce solute diffusivity and partitioning: implications for the chondrocyte biological response. *J Biomech* 2001;34-11:1463-9.
28. Quinn T M, Kocian P, Meister J J. Static compression is associated with decreased diffusivity of dextrans in cartilage explants. *Arch Biochem Biophys* 2000;384-2:327-34.
29. Lutolf M P, Hubbell J A. Synthesis and physicochemical characterization of end-linked poly(ethylene glycol)-co-peptide hydrogels formed by Michael-type addition. *Biomacromolecules* 2003;4-3:713-22.
30. Staskus P W, Masiarz F R, Pallanck L J, Hawkes S P. The 21-kDa protein is a transformation-sensitive metalloproteinase inhibitor of chicken fibroblasts. J Biol Chem 1991; 266(1):449-54.
31. Negro A, Onisto M, Grassato L, Caenazzo C, Garbisa S. Recombinant human TIMP-3 from *Escherichia coli*: synthesis, refolding, physico-chemical and functional insights. Protein Eng 1997;10(5):593-9.
32. Kashiwagi M, Tortorella M, Nagase H, Brew K. TIMP-3 is a potent inhibitor of aggrecanase 1 (ADAM-TS4) and aggrecanase 2 (ADAM-TS5). J Biol Chem 2001;276(16): 12501-4.

This application discloses various inventive embodiments that each have certain features. In general, these features may be mixed-and-matched with each other to create additional functional embodiments.

The invention claimed is:

1. A fusion polypeptide comprising a therapeutic agent and the amino acid sequence consisting of SEQ ID NO: 1, SEQ ID NO: 2 or SEQ ID NO: 3, wherein the amino acid sequence specifically binds a cartilage tissue.

2. The polypeptide of claim 1 wherein the therapeutic agent comprises a tissue inhibitor of matrix metalloproteinases-3 (TIMP-3) polypeptide.

3. A delivery system for targeting a therapeutic agent to a cartilage comprising:
   a substantially purified preparation that comprises a pharmaceutically acceptable excipient, a therapeutic agent, and a polypeptide ligand consisting of an amino acid sequence selected from the group consisting of SEQ ID NO: 1, SEQ ID NO: 2 and SEQ ID NO: 3, that specifically binds a cartilage tissue, wherein the polypeptide ligand is bound to the therapeutic agent for targeted delivery of the therapeutic agent to cartilage tissue.

4. The delivery system of claim 3 wherein the therapeutic agent comprises a drug, a visualization agent, or a therapeutic polypeptide.

5. The delivery system of claim 3 wherein the polypeptide ligand and the therapeutic agent are a fusion polypeptide.

6. The delivery system of claim 5 wherein the therapeutic agent comprises a matrix metalloproteinase inhibitor.

7. The delivery system of claim 3 comprising covalent bonds between the polypeptide ligand and the therapeutic agent.

8. The delivery system of claim 3 wherein the polypeptide ligand is covalently bonded to a biocompatible polymer that is associated with the therapeutic agent.

9. The delivery system of claim 8 wherein the biocompatible polymer is free of amino acids.

10. The delivery system of claim 3 wherein the therapeutic agent is hyaluronic acid, chondroitin sulfate, or keratan sulfate.

11. The delivery system of claim 3 comprising a collection of nanoparticles that comprise the therapeutic agent and the polypeptide ligand.

12. The delivery system of claim 3 further comprising a polymer free of amino acids that has a molecular weight of at least 500 Daltons.

13. The delivery system of claim 12 wherein the polymer comprises at least 400 Da of polyethylene glycol.

14. The fusion polypeptide of claim 1 further comprising a synthetic backbone linkage.

15. The fusion polypeptide of claim 1 wherein the therapeutic agent comprises chondroitin sulfate, keratin sulfate, or hyaluronic acid.

16. A method of treating cartilage of a mammal comprising administering to the mammal a pharmaceutically acceptable composition that comprises the fusion polypeptide of claim 1, that targets the therapeutic agent to the cartilage tissue by specific binding of the amino acid sequence to the cartilage tissue of the mammal.

17. The method of claim 16 wherein the composition is administered intra-articularly.

18. The method of claim 16 wherein the pharmaceutically acceptable composition further comprises a pharmaceutically acceptable excipient.

\* \* \* \* \*

SEQUENCE LISTING

```
<160> NUMBER OF SEQ ID NOS: 18

<210> SEQ ID NO 1
<211> LENGTH: 6
<212> TYPE: PRT
<213> ORGANISM: mammalian

<400> SEQUENCE: 1

Trp Tyr Arg Gly Arg Leu
1               5

<210> SEQ ID NO 2
<211> LENGTH: 6
<212> TYPE: PRT
<213> ORGANISM: mammalian

<400> SEQUENCE: 2

Asp Pro His Phe His Leu
1               5

<210> SEQ ID NO 3
<211> LENGTH: 6
```

```
<212> TYPE: PRT
<213> ORGANISM: mammalian

<400> SEQUENCE: 3

Arg Val Met Leu Val Arg
1               5

<210> SEQ ID NO 4
<211> LENGTH: 7
<212> TYPE: PRT
<213> ORGANISM: mammalian

<400> SEQUENCE: 4

Trp Tyr Arg Gly Arg Leu Cys
1               5

<210> SEQ ID NO 5
<211> LENGTH: 19
<212> TYPE: DNA
<213> ORGANISM: mammalian

<400> SEQUENCE: 5
catgtaccgt aacactgag                                               19

<210> SEQ ID NO 6
<211> LENGTH: 6
<212> TYPE: PRT
<213> ORGANISM: mammalian

<400> SEQUENCE: 6

Tyr Arg Leu Gly Arg Trp
1               5

<210> SEQ ID NO 7
<211> LENGTH: 7
<212> TYPE: PRT
<213> ORGANISM: mammalian

<400> SEQUENCE: 7

Tyr Arg Leu Gly Arg Trp Cys
1               5

<210> SEQ ID NO 8
<211> LENGTH: 9
<212> TYPE: PRT
<213> ORGANISM: mammalian

<400> SEQUENCE: 8

Gly Gly Gly Trp Tyr Arg Gly Arg Leu
1               5

<210> SEQ ID NO 9
<211> LENGTH: 45
<212> TYPE: DNA
<213> ORGANISM: mammalian

<400> SEQUENCE: 9
ctgatgcggc cgctctcaca gcctgcccct ataccagccg ccgcc                  45

<210> SEQ ID NO 10
<211> LENGTH: 9
<212> TYPE: PRT
<213> ORGANISM: mammalian

<400> SEQUENCE: 10
```

Trp Tyr Arg Gly Arg Leu Gly Gly Gly
1               5

<210> SEQ ID NO 11
<211> LENGTH: 42
<212> TYPE: DNA
<213> ORGANISM: mammalian

<400> SEQUENCE: 11
atcaggagcg gccgctggta tagggcagg ctgggcggcg gc                    42

<210> SEQ ID NO 12
<211> LENGTH: 42
<212> TYPE: DNA
<213> ORGANISM: mammalian

<400> SEQUENCE: 12
ctgatgcggc cgctcaagat ggaaatgagg atcgccgccg cc                   42

<210> SEQ ID NO 13
<211> LENGTH: 9
<212> TYPE: PRT
<213> ORGANISM: mammalian

<400> SEQUENCE: 13

Asp Pro His Phe His Leu Gly Gly Gly
1               5

<210> SEQ ID NO 14
<211> LENGTH: 42
<212> TYPE: DNA
<213> ORGANISM: mammalian

<400> SEQUENCE: 14
ctgatgcggc cgctcacgaa caagcataac acggccgccg cc                   42

<210> SEQ ID NO 15
<211> LENGTH: 9
<212> TYPE: PRT
<213> ORGANISM: mammalian

<400> SEQUENCE: 15

Arg Val Met Leu Val Arg Gly Gly Gly
1               5

<210> SEQ ID NO 16
<211> LENGTH: 18
<212> TYPE: DNA
<213> ORGANISM: mammalian

<400> SEQUENCE: 16
tggtataggg gcaggctg                                              18

<210> SEQ ID NO 17
<211> LENGTH: 18
<212> TYPE: DNA
<213> ORGANISM: mammalian

<400> SEQUENCE: 17
aagatggaaa tgaggatc                                              18

<210> SEQ ID NO 18
<211> LENGTH: 18

```
<212> TYPE: DNA
<213> ORGANISM: mammalian

<400> SEQUENCE: 18
acgaacaagc ataacacg                                                  18
```